United States Patent
Ohta et al.

(10) Patent No.: US 7,052,682 B2
(45) Date of Patent: May 30, 2006

(54) COMPOSITION FOR BLENDING TO HAIR TREATING AGENTS AND A HAIR TREATING AGENT

(75) Inventors: Toshio Ohta, Kita-ku (JP); Michihiro Aga, Kita-ku (JP); Katsuhiro Watanabe, Kita-ku (JP)

(73) Assignee: San-Ei Kagaku Co., Ltd., Tokyo (JP)

( * ) Notice: Subject to any disclaimer, the term of this patent is extended or adjusted under 35 U.S.C. 154(b) by 0 days.

(21) Appl. No.: 10/998,928

(22) Filed: Nov. 30, 2004

(65) Prior Publication Data

US 2005/0095214 A1    May 5, 2005

Related U.S. Application Data

(63) Continuation of application No. 10/106,361, filed on Mar. 27, 2002, now Pat. No. 6,835,375.

(30) Foreign Application Priority Data

Mar. 30, 2001  (JP)  ............................. 2001-99821
Mar. 30, 2001  (JP)  ............................. 2001-99824

(51) Int. Cl.
*A61K 7/09*    (2006.01)
*A61K 7/06*    (2006.01)

(52) U.S. Cl. ............... 424/70.19; 424/70.2; 424/70.12; 424/70.27; 424/70.31

(58) Field of Classification Search ............... 424/90.1, 424/70.11, 70.12
See application file for complete search history.

(56) References Cited

U.S. PATENT DOCUMENTS

| 5,601,620 | A | * | 2/1997 | Ishikawa | ........................ 8/405 |
| 5,911,979 | A |   | 6/1999 | Midha et al. | |
| 6,419,962 | B1 |   | 7/2002 | Yokoyama et al. | |
| 2002/0037266 | A1 | * | 3/2002 | Terazaki et al. | ......... 424/70.12 |
| 2002/0106387 | A1 | * | 8/2002 | Nishida et al. | ............. 424/401 |

OTHER PUBLICATIONS

Harry's Cosmeticology by Ralph Harry, pp. 431-441, 1982.
Skin Care and Cosmetic Ingredients Dictionary, p. 90, 1994.

* cited by examiner

*Primary Examiner*—Jyothsna Venkat
(74) *Attorney, Agent, or Firm*—Sherman & Associates

(57) ABSTRACT

The present invention provides compositions for blending in hair treating agents which can prepare hair conditioners, waving agents, finishing agents or thickening agents used on preparing hair treating agents easily by lower cost. Further, the present invention provides hair treating agents which are excellent in the features of feeling at actual use such as moist feel, slippery feel, slightly oily feel, good feeling to hair, brilliance, suppleness, soft feel and smooth combing and excellent in the features of hair treating agents such as less damage for hair (protective ability of hair), absorbency•penetration•fixing ability•spreading ability, wetting ability and smooth forming of wave without unevenness and tight and protection for generation of static electricity, by containing cationic surfactants or nonionic surfactants.

13 Claims, No Drawings

US 7,052,682 B2

COMPOSITION FOR BLENDING TO HAIR TREATING AGENTS AND A HAIR TREATING AGENT

CROSS REFERENCE TO RELATED APPLICATION

This application is a continuation of application U.S. Ser. No. 10/106,361, filed Mar. 27, 2002 now U.S. Pat. No. 6,835,375, which claims foreign priority to JP 2001-099821, filed Mar. 30, 2001 and JP 2001-099824, filed Mar. 30, 2001.

FIELD OF THE INVENTION

The present invention relates to compositions for blending in hair treating agents, and also the hair treating agents. Especially, the present invention relates to compositions to be blended in hair treating agents, and also the present invention relates to the hair treating agents prepared therefrom such as hair conditioners (including hair treatments and rinses etc.), hair colorings, waving agents, finishing agents, emulsion stabilizers, permanent waving iron sliding improvers and thickening agents used on preparing hair treating agents.

DESCRIPTION OF THE PRIOR ART

Recently, the beauty sense required to hair is becoming more serious, and along with said requirement, the requirement to a heir treating agent is also becoming serious. Therefore, hair treating agents, which are excellent in feels when used such as luster, smooth feel, neat feel, soft feel, moisture feel, rustle feeling, less stickiness, slightly oily feel, pleasant sense of touch to the hair, suppleness and smooth combing, as well as functionalities such as absorptivity of hair treating agents to hair, penetrating ability of hair treating agents into hair, adhesiveness of hair treating agents to hair, spreadability of hair treating agents, moisturizing ability, protective ability for hair (less hair damage), smooth formation of firmly rooted and knitted wave and prevention against generation of static electricity, are more strongly required.

For the purpose to satisfy the above-mentioned requirement of the consumer, hair treating agents such as hair conditioners, hair colorings, waving agents, finishing agents, emulsion stabilizers, permanent waving iron sliding improvers and thickening agents used on preparing hair treating agents, in which various effective ingredients were contained, have been proposed.

However, at the preparation of the conventional hair treating agents, the processes are complicated and take long time and high cost because each ingredient must be respectively weighed, added and blended, and these processes are considered as a serious problem.

Further, in the conventional hair treating agents, the specific ingredients, for example, fatty esters, surfactants or silicones (Si compounds) are blended to the hair treating agents.

However, these compounds are not popular because they have specific chemical structures. Therefore, these materials have a problem that they are difficult to purchase in the market and are expensive. Further, these materials have also a problem that the hair treatments effects are not sufficient.

SUMMARY OF THE INVENTION

The object of the present invention is to provide compositions for blending in hair treating agents, which can prepare hair treating agents including, for example, hair conditioners (such as hair treatments and rinses etc.), hair colorings, waving agents, finishing agents, thickening agents used on preparing hair treating agents, emulsion stabilizers and permanent waving iron sliding improvers, easily and by lower cost. Further, the object of the present invention is to provide the hair treating agents, which are excellent feels when used such as luster, smooth feel, neat feel, soft feel, moisture feel, rustle feeling, less stickiness, slightly oily feel, pleasant sense of touch to the hair, suppleness and smooth combing, as well as functionalities such as absorptivity of hair treating agents to hair, penetrating ability of hair treating agents into hair, adhesiveness of hair treating agents to hair, spreadability of hair treating agents, moisturizing ability, protective ability for hair (less hair damage), smooth formation of firmly rooted and knitted wave and prevention against generation of static electricity.

For the purpose to dissolve above-mentioned problems, the inventors of the present invention have conduced an ardent study and have found out that the use of compositions for blending in hair treating agents, in which at least one compound, especially one or two compounds selected from the group consisting of nonionic surfactants, silicones and polymers were contained, could prepare hair treating agents having the above-mentioned excellent hair treating effect (i.e. excellent feels when used as well as functionalities) easily and by lower cost, and accomplished the present invention.

That is, the present invention provides compositions for blending in hair treating agents, which contain at least one compound selected from the group consisting of nonionic surfactants, silicones and polymers.

Further, the present invention provides the hair treating agents in which the above-mentioned compositions are blended.

Now, the present inventions will be described according to the following embodiment and Examples.

DETAILED DESCRIPTION OF PREFERRED EMBODIMENTS

The First Embodiment

In this embodiment, at least one compound, for example, one or two compounds selected from the group consisting of nonionic surfactants, silicones and polymers are contained in the compositions for blending in hair treating agents of the present invention.

Examples of nonionic surfactants include, for example, polyoxyethylene alkyl ethers, polyoxyethylene alkenyl ethers, polyoxyethylene alkyl aryl ethers, polyoxyethylene derivatives prepared from natural fatty acids, (mono- or sesqui-) esters prepared with polyhydric alcohols (e.g. sorbitanes etc.) and higher fatty acids, fatty acid alkylolamides and ethylene oxide-propylene oxide block copolymers.

Ehylene oxide (EO) addition polymerization degrees in "polyoxyethylene" may be, for example, 10~70. Propylene oxide (PO) addition polymerization degrees in "polyoxypropylene" may be, for example, 3~90.

Concrete examples of nonionic surfactants include one to four compounds selected from the group consisting of polyoxyethylene lauryl ether, polyoxyethylene cetyl ether, polyoxyethylene oleyl ether, polyoxyethylene noriylphenyl ether, polyoxyethylene lanolin, polyoxyethylene hydrogenated castor oil, sorbitan monostearate, sorbitan monooleate, sorbitan sesquioleate, polyoxyethylene sorbitan monooleate, oleic acid diethanolamide and polyoxyethylene polyoxypropylene glycol.

For example, in compositions for blending in hair colorings, in compositions for blending in waving agents, in compositions for blending in finishing agents and in compositions for blending in emulsion stabilizers, polyoxyethylene oleyl ether may be contained.

In compositions for blending in hair colorings, in compositions for blending in waving agents, in compositions for blending in finishing agents and in compositions for blending in emulsion stabilizers, sorbitan monooleate may be contained.

Example of silicones (Si compounds) include silicone oils. Examples of silicone oils include siloxanes, their homopolymers and copolymers. The polymerization degrees of polysilicones are not limited. Polysilicones between low polymerized polysilicones and highly polymerized polysilicones may be used.

Concrete examples of silicones include, one to three compounds selected from the group consisting of decamethyl cyclopentasiloxane, methyl polysiloxane, methylphenyl polysiloxane, dimethylsiloxane•methylstearoxysiloxane copolymer and aminoethylaminopropylsiloxane•dimethylsiloxane copolymer.

For example, in compositions for blending in waving agents and in compositions for blending in permanent waving iron sliding improvers, decamethyl cyclopentasiloxane may be contained.

In compositions for blending in hair colorings and in compositions for blending in waving agents, for example, methyl polysiloxane may be contained.

Concrete examples of polymers include one or three compounds selected from the group consisting of carboxyvinylpolymer (average molecular weight, e.g. 1 million~5 million), polyethylene glycol (average molecular weight, e.g. 1 million~5 million), styrene polymer, polyvinylpyrrolidone (average molecular weight, e.g. 100000~1 million), and hydroxyethyl cellulose (the degree of viscosity of 2% aqueous solution, e.g. 1000~20000 cps.).

For example, in compositions for blending in hair colorings, in compositions for blending in waving agents and in compositions for blending in finishing agents, polymers may be contained.

Further, in the compositions for blending in hair treating agents of the present invention, any kind of additives may be contained in accordance with the kind and the purposes of hair treating agents. For example, in the composition for blending in hair treating agent of the present invention, two to seven ingredients selected from the group consisting of fats and oils, paraffins•waxes, anionic surfactants, organic acids, amphoteric surfactants, phosphoric acids, bases, sequestering agents, antioxidants, parabens and water may be contained.

Examples of fats and oils include, for example, animal fats and oils and vegetable fats and oils. Concrete examples of fats and oils include one to three compounds selected from the group consisting of olive oil, safflower oil, castor oil, lanolin, hydrogenated oil (hydrogenated palm oil fatty acid triglyceride, hydrogenated tallow acid triglyceride, hydrogenated castor oil etc.) and mink oil.

For example, in compositions for blending in hair colorings, in compositions for blending in waving agents, in compositions for blending in finishing agents, in compositions for blending in emulsion stabilizers and in compositions for blending in permanent waving iron sliding improvers, fats and oils may be contained.

Examples of paraffins•waxes include paraffin itself, wax itself and their derivatives (e.g. their halides). Concrete examples of paraffins•waxes include one or two compounds selected from the group consisting of liquid petrolatum, light liquid isoparaffin, chlorinated paraffin and microcrystalline wax.

For example, in compositions for blending in hair colorings, in compositions for blending in waving agents, in compositions for blending in finishing agents and in compositions for blending in emulsion stabilizers, paraffins•waxes may be contained.

Examples of anionic surfactants include, for example, salts of polyoxyethylene alkyl ether sulfates. Concrete examples of anionic surfactants include ammonium polyoxyethylene lauryl ether sulfate or triethanolamine polyoxyethylene lauryl ether sulfate. For example, in compositions for blending in waving agents, anionic surfactants may be contained. EO addition polymerization degrees of abovementioned "polyoxyethylene" may be, for example, 1 to 5.

Examples of organic acids include fatty acids. Concrete examples of organic acids include one or two compounds selected from the group consisting of lauric acid, stearic acid, oleic acids and sorbic acid.

For example, in compositions for blending in hair colorings, in compositions for blending in waving agents, in compositions for blending in finishing agents and in compositions for blending in emulsion stabilizers, organic acids may be contained.

Examples of amphoteric surfactants include carboxylic acid type betaines. Concrete examples of amphoteric surfactants include 2-alkyl-N-carboxymethyl-N-hydroxyethyl imidazolinium betaine and/or cocoyl amide propyldimethyl glycine. For example, in compositions for blending in waving agents, amphoteric surfactants may be contained.

Examples of phosphoric acids include phosphoric acid itself and its partially neutralized salts. Concrete examples of phosphoric acids include one or two compounds selected from the group consisting of phosphoric acid, dibasic sodium phosphate and monobasic sodium phosphate.

For example, in compositions for blending in hair colorings, in compositions for blending in waving agents, in compositions for blending in finishing agents and in compositions for blending in emulsion stabilizers, phosphoric acids may be contained.

Examples of bases include amines and alkaline metal hydroxides. Concrete examples of bases include triethanolamine or sodium hydroxide. For example, in compositions for blending in hair colorings, in compositions for blending in waving agents, in compositions for blending in finishing agents and in compositions for blending in emulsion stabilizers, bases may be contained.

Concrete examples of sequestering agents include 1-hydroxyethane-1,1-diphosphonic acid or disodium edetate. For example, in compositions for blending in hair colorings, in compositions for blending in waving agents and in compositions for blending in finishing agents, sequestering agents may be contained.

Concrete examples of antioxidants include dibutylhydroxytoluene.

For example, in compositions for blending in permanent waving iron sliding improvers, antioxidants may be contained.

Examples of parabens include parahydroxybenzoates. Concrete examples of parabens include propyl parahydroxybenzoate and/or methyl parahydroxybenzoate. For example, in compositions for blending in waving agents, parabens may be contained.

In the formulations of the compositions for blending in hair treating agents of the present invention, when the content of one or two kinds selected from the group consisting of nonionic surfactants, silicones and polymers is A (wt %), it is desirable for A to satisfy following expression; $0.1 \leq A \leq 100$.

For example, in a case of the compositions for blending in hair conditioners, A may be $80 \leq A \leq 100$.

For example, in a case of compositions for blending in hair colorings, A may be $0.5 \leq A \leq 20$.

For example, in a case of compositions for blending in waving agents and in compositions for blending in emulsion stabilizers, A may be $0.1 \leq A \leq 100$.

For example, in a case of compositions for blending in finishing agents, A may be $0.5 \leq A \leq 50$.

For example, in a case of compositions for blending in permanent waving iron sliding improvers, A may be $5 \leq A \leq 30$.

As the substantial method to prepare the compositions for blending in hair treating agents of this embodiment, following method may be exemplified. That is, one or two kinds selected from the group consisting of nonionic surfactants, silicones and polymers and, If necessary, ingredients such as additives are mixed homogeneously with stirring under heating (If necessary). The adding order of each ingredient is not limited. For example, all ingredients may be added at a time. Or, each ingredient may be added in such order as following ingredient is added after the previously added ingredients have been dissolved completely.

In another preparation method of the compositions for blending in hair treating agents of this embodiment, for example, oiliness ingredients containing one or two kinds selected from the group consisting of nonionic surfactants, silicones and polymers are stirred and mixed homogeneously under heating if necessary. Next, water, which has been heated if necessary, is added to this homogeneous mixture (or this homogeneous mixture is added to water), and then mixed homogeneously as stirring to be emulsified. And then, remaining aqueous ingredients are added to prepare the compositions for blending in hair treating agents of this embodiment.

The hair treating agents of the present invention contain the above-mentioned compositions for blending in hair treating agents of the present invention. Hair conditioners, hair colorings, waving agents, finishing agents, emulsion stabilizers and permanent waving iron sliding improvers are illustrated below as the hair treating agents.

The hair conditioners of the present invention contain above-mentioned compositions for blending in hair conditioners. One or more kinds of the compositions for blending in hair conditioners may be used.

Further, in the hair conditioners of the present invention, additive compositions and water may be contained. Examples of additive compositions include mixtures with alcohols and cationic surfactants.

In the formulations of the hair conditioners of the present invention, the contents of the compositions for blending in hair conditioners are, for example, from 1 to 20 wt. %.

The preparing methods of the hair conditioners of the present invention are not limited. For example, the compositions for blending in hair conditioners and additive compositions are dissolved homogeneously under heating. To this homogeneously dissolved material, water are added and mixed homogeneously to prepare the hair conditioner of the present invention.

Hair colorings of the present invention include oxidizing hair coloring agents. The oxidizing hair coloring agents may be composed of No.1 agents and No.2 agents (In the present invention, No.1 agents alone and No.2 agents alone are also included in the hair colorings of the present invention.). No.1 agents of the oxidizing hair coloring agents of the present invention may contain alkaline agents, dye intermediates and water may be contained besides the compositions for blending in hair colorings of the present invention.

Examples of alkaline agents include ammonia aqueous solution and monoethanolamine (MEA). Examples of dye intermediates include, for example, phenylene diamines (e.g. ortho-, meta-, para-phenylene diamine), phenols (e.g. ortho-, meta-, para-aminophenol and nitrophenols), resorcinol and aminocresols.

In the formulations of No.1 agents of oxidizing hair coloring agents, the contents of the compositions for blending in hair colorings are, for example, from 20 to 60 wt. %.

As the substantial methods to prepare No.1 agents of oxidizing hair coloring agents, following methods may be exemplified. That is, for example, dye intermediates is added to heated water to be dissolved homogeneously, and then the composition for blending in hair colorings is added and mixed homogeneously. After cooled, alkaline agent is added with stirring to prepare No.1 agents of oxidizing hair coloring agent. The heating temperatures of water and the composition for blending in hair coloring are desirably lower than decomposition temperatures of the ingredients, for example, lower than 95° C.

No.2 agents of oxidizing hair coloring agents of the present invention may contain sequestering agents, pH adjustors, oxidizing agents and water may be contained besides the compositions for blending in hair colorings of the present invention. Examples of sequestering agents include 1-hydroxyethane-1,1-diphosphonic acid. Examples of pH adjustors include phosphoric acids (for example, dibasic sodium phosphate). Examples of oxidizing agents include hydrogen peroxide.

In formulations of No.2 agents of oxidizing hair coloring agents, for example, 0.5–15 wt. % of the compositions for blending in hair colorings maybe contained.

As the substantial methods to prepare No.2 agents of oxidizing hair coloring agents, following method may be exemplified. That is, for example, the composition for blending in hair coloring, sequestering agent, pH adjustor, oxidizing agent and water are mixed homogeneously with stirring under heating, if necessary, to prepare No.2 agent of oxidizing hair coloring agent.

The oxidizing hair coloring agents of the present invention contain at least one selected from the group consisting of No.1 agents of oxidizing hair coloring agents of the present invention and No.2 agents of oxidizing hair coloring agents of the present invention. For example, in the oxidizing hair coloring agents of the present invention, the hair colorings consisting of No.1 agents of oxidizing hair coloring agents of the present invention and No.2 agents of oxidizing hair coloring agents of the present invention, the hair colorings consisting of No.1 agents of oxidizing hair coloring agents of the present invention and No.2 agents of oxidizing hair coloring agents except the above-mentioned ones, and the hair colorings consisting of No.1 agents of oxidizing hair coloring agents except the above-mentioned ones and No.2 agents of oxidizing hair coloring agents of the present invention are included. "No.1 agents of oxidizing hair coloring agents except the above-mentioned ones" and "No.2 agents of oxidizing hair coloring agents except the above-mentioned ones" include such No.1 agents and No.2 agents as are generally used for the usual hair colorings.

Another hair treating agents of the present invention include decolorizing agents. The decolorizing agents may be composed of No.1 agents and No.2 agents (the decolorizing agents, No.1 agents alone and No.2 agents alone are included in the hair colorings of the present invention). No.1 agents of the decolorizing agents of the present invention may contain alkaline agents and water besides the compositions for blending in hair colorings of the present invention. Examples of alkaline agents include ammonia and MEA.

In formulations of No.1 agents of decolorizing agents, the contents of the compositions for blending in hair colorings may be, for example, from 20 to 60 wt. %.

As the substantial method to prepare No.1 agents of decolorizing agents, following method may be exemplified. That is, for example, the composition for blending in hair coloring of the present invention, that has been heated and dissolved homogeneously, is added with stirring to heated water to be emulsified. After cooling, additives such as alkaline agent are added to prepare No.1 agent of decolorizing agent. The heating temperatures of water and the composition for blending in hair coloring are desirably lower than the decomposition temperatures of the ingredients, for example, lower than 95° C.

Ingredients, formulations and preparation methods of No.2 agents of decolorizing agents of the present invention may be the same as No.2 agents of oxidizing hair coloring agents of the present invention.

The decolorizing agents of the present invention contain at least one selected from the group consisting of No.1 agents of decolorizing agents of the present invention and No.2 agents of decolorizing agents of the present invention. For example, in the decolorizing agents of the present invention, the decolorizing agents consisting of No.1 agents of decolorizing agents of the present invention and No.2 agents of decolorizing agents of the present invention, the decolorizing agents consisting of No.1 agents of decolorizing agents of the present invention and No.2 agents of decolorizing agents except the above-mentioned ones, and the decolorizing agents consisting of No.1 agents of decolorizing agents except the above-mentioned ones and No.2 agents of decolorizing agents of the present invention are included. "No.1 agents of decolorizing agents except the above-mentioned ones" and "No.2 agents of decolorizing agents except the above-mentioned ones" include such No.1 agents and No.2 agents as are generally used for the usual decolorizing.

Waving agents of the present invention may be composed of No.1 agents and No.2 agents (In the present invention, both No.1 agents alone and No.2 agents alone are also included in the hair treating agents of the present invention). No.1 agents of the waving agents of the present invention may contain additive compositions, reducing agents, alkaline agents and water besides the compositions for blending in waving agents of the present invention.

One or more kinds of the compositions for blending in waving agents may be used. Examples of the additive compositions include, for example, mixtures comprised of various kinds of surfactants (nonionic surfactants, amphoteric surfactants and anionic surfactants), sequestering agents, amines, alcohols and water. Examples of the reducing agents include thioglycolic acid and cysteine or their salts [ammonium salt, monoethanolamine (MEA) salt, hydrochloric acd salts etc.]. Examples of the alkaline agents include ammonia, amines (MEA, triethanolamine, isopropanolamine, etc.), ammonium salts (ammonium bicarbonate etc.) and basic amino acid.

In formulations of No.1 agents of the waving agents of the present invention, the contents of the compositions for blending in waving agents may be, for example, 0.5–70 wt. %.

As the substantial method to prepare No.1 agents of the present waving agents, following method may be exemplified. That is, for example, each ingredient is mixed with stirring under heating, if necessary, to prepare No.1 agents. Adding order of each ingredient is not limited. For example, each ingredient may be added at a time. Or, for example, the compositions for blending in waving agents, water, alkaline agents and reducing agents may be added in this order.

In No.2 agents of the waving agents of the present invention, additive compositions, oxidizing agents, alkaline agents and water etc. may be contained besides the compositions for blending in waving agents of the present invention. Examples of the additive compositions include the ones exemplified in No.1 agents of the waving agents. Examples of the oxidizing agents include salts of bromic acid (e.g. sodium bromate) and hydrogen peroxide. Examples of alkaline agents include alkaline metal hydroxides (e.g. sodium hydroxide).

In formulations of No.2 agents of the waving agents, the contents of the compositions for blending in waving agents may be, for example, 0.5–70 wt. %.

As the substantial method to prepare No.2 agents of the present waving agents, following method may be exemplified. That is, for example, each ingredient is mixed with stirring under heating, if necessary, to prepare No.2 agents. Adding order of each ingredient is not limited. For example, each ingredient may be added at a time. Or, for example, the compositions for blending in waving agents, water, oxidizing agent and alkaline agents may be added in this order.

The waving agents of the present invention contain at least one selected from the group consisting of No.1 agents of waving agents of the present invention and No.2 agents of waving agents of the present invention. For example, the waving agents of the present invention is one consisting of No.1 agents of waving agents of the present invention and No.2 agents of waving agents of the present invention, one consisting of No.1 agents of waving agents of the present invention and No.2 agents of waving agents except the above-mentioned ones, and another one consisting of No.1 agents of waving agents except the above-mentioned ones and No.2 agents of waving agents of the present invention.

"No.1 agents of waving agents except the above-mentioned ones" and "No.2 agents of waving agents except the above-mentioned ones" include such No.1 and No.2 agents as are ordinary used in the conventional waving agents.

The finishing agents of the present invention contain the compositions for blending in finishing agents, and may further contain alcohols, alkaline agents, silicones, amines, organic acids, esters, cationic surfactants, hydrolyzed animal protein, colorants, parabens and perfumes.

Examples of alcohols include lower and higher alcohols (e.g. ethanol, cetanol, behenyl alcohol), aromatic alcohols (e.g. phenoxyethanol), glycols (e.g. propylene glycol, 1,3-butylene glycol, neopentyl glycol dicaprate). Examples of alkaline agents include alkaline metal hydroxides (e.g. sodium hydroxide). Examples of silicones, organic acids and parabens include respectively the ones exemplified in the aforementioned compositions for blending in hair treating agents.

Examples of amines include MEA. Examples of esters include fatty esters (e.g. isononyl isononanoate, polyoxyethylene distearate). Examples of cationic surfactants include aliphatic alkyl trimethyl ammonium salts (e.g. stearyl trimethyl ammonium chloride). Examples of colorants include tar colorants (e.g. Blue No.1). Examples of perfumes include such ones as are ordinary used in the usual finishing agents.

In formulations of the finishing agents of the present invention, the contents of the compositions for blending in finishing agents may be, for example, 1~70 wt. %.

As the substantial methods to prepare the finishing agents of the present invention, following method may be exemplified. That is, for example, each ingredient is mixed homogeneously as stirring to prepare the finishing agents. All ingredients may be added at a time. Or, all ingredients may be added in such order as each ingredient can be dissolved homogeneously. Concretely, the compositions for blending in finishing agents, water, alcohols and colorants are mixed homogeneously with stirring, and then further parabens, alkaline agents and silicones are added in order and mixed homogeneously as stirring to prepare the finishing agents.

In another preparation method of finishing agents of the present invention, for example, alkaline agents, water and esters are mixed with stirring under heating to prepare aqueous solutions. On the other hand, the composition for blending in finishing agent, parabens and remaining oiliness ingredients are mixed with stirring under heating to prepare homogeneous mixture. Next, the homogeneous mixture is added to the above-mentioned aqueous solutions, and then emulsified with stirring to prepare the finishing agents.

In another preparation method of finishing agents of the present invention, for example, the heated composition for blending in finishing agent are added to heated water to prepare emulsion. After cooling, the above-mentioned emulsion and amines are added in order to another composition for blending in finishing agent, and then mixed homogeneously with stirring to prepare the finishing agents.

Emulsion stabilizers of the present invention are such ones as are blended to emulsion in order to improve the emulsion stability when emulsion such as waving agents is added to concentrated salts materials. Emulsion stabilizers of the present invention may be the compositions for blending in emulsion stabilizers themselves.

The contents of the emulsion stabilizers of the present invention may be, for example, 5~20 parts by weight per 100 parts by weight of the waving agents.

Permanent waving iron sliding improvers of the present invention contain the compositions for blending in permanent waving iron sliding improvers, and may further contain additives such as perfumes and colorants. Examples of perfumes include such ones as are ordinarily used in usual permanent waving iron sliding improvers. Examples of colorants include tar colorants.

In formulations of the permanent waving iron sliding improvers of the present invention, the contents of the compositions for blending in permanent waving iron sliding improvers may be, for example, more than 80 wt. %.

As the substantial methods to prepare the permanent waving iron sliding improvers of the present invention, following method may be exemplified. That is, for example, the compositions for blending in permanent waving iron sliding improvers and additives are mixed homogeneously as stirring under heating, if necessary, to prepare the permanent waving iron sliding improvers.

The Second Embodiment

In this embodiment, cationic surfactants bedsides at least one compound (for example, nonionic surfactants) selected from the group consisting of nonionic surfactants, silicones and polymers are contained in the compositions for blending in hair treating agents of the present invention.

Examples of cationic surfactants include, for example, dipolyoxyethylene alkyl methyl ammonium salts, dipolyoxyethylene alkenyl methyl ammonium salts, alkyl trimethyl ammonium salts, alkenyl trimethyl ammonium salts, fatty acid amidoalkyl ethyl dimethyl ammonium salts.

Concrete examples of cationic surfactants include one to three compounds selected from the group consisting of dipolyoxyethylene [e.g. 2~10 EO] oleyl methyl ammonium chloride, lauryl trimethyl ammonium chloride, lauryl trimethyl ammonium bromide, cetyl trimethyl ammonium chloride, stearyl trimethyl ammonium chloride, cethyl trimethyl ammonium saccarinate and lanolin amidopropyl ethyl dimethyl ammonium ethylsulfate.

For example, in compositions for blending in hair conditioners, in compositions for blending in waving agents and in compositions for blending in finishing agents, dipolyoxyethylene oleyl methyl ammonium chloride may be contained. In compositions for blending in waving agents, for example, lauryl trimethyl ammonium chloride may be contained. In compositions for blending in hair conditioners and in compositions for blending in waving agents, for example, cetyl trimethyl ammonium chloride may be contained.

In this embodiment, nonionic surfactants are contained in the compositions for blending in hair treating agents of the present invention. Examples of nonionic surfactants include, for example, polyoxyethylene alkyl ethers, polyoxyethylene alkenyl ethers, polyoxyethylene aryl ethers, polyoxyethylene derivatives prepared from natural fatty acids, ethylene oxide-propylene oxide block copolymers, fatty acid alkylolamides and esters (e.g. mono-, di- or trimesters) prepared with polyhydric alcohols (e.g. glycols and sorbitanes etc.) and higher fatty acids.

Ethylene oxide (EO) addition polymerization degrees in "polyoxyethylene" may be, for example, 2~70. Propylene oxide (PO) addition polymerization degrees in "polyoxypropylene" may be, for example, 10~20.

Concrete examples of nonionic surfactants include one to four compounds selected from the group consisting of polyoxyethylene lauryl ether, polyoxyethylene cetyl ether, polyoxyethylene oleyl ether, polyoxyethylene nonylphenyl ether, polyoxyethylene castor oil, polyoxyethylene lanolin, polyoxyethylene•polyoxpropylene lanolin, lauric acid diethanolamide, polyethylene glycol monolaurate, polyoxyethylene glyceryl oleate, sorbitan monolaurate and sorbitan trioleate.

For example, in compositions for blending in waving agents, polyoxyethylene lauryl ether may be contained. In compositions for blending in waving agents and in compositions for blending in thickening agents used on preparing hair treating agents, for example, polyoxyethylene nonylphenyl ether may be contained. In compositions for blending in hair conditioners and in compositions for blending in waving agents, for example, polyoxyethylene lanolin and/or lauric acid diethanolamide may be contained.

Further, in the compositions for blending in hair treating agents of the present invention, any kind of additives may be contained in accordance with the kind and the purposes of hair treating agents. For example, in the composition for blending in hair treating agent of the present invention, one to five kinds of ingredients selected from the group consisting of fats and oils, hydrocarbons, silicones (Si compounds), alkalis, acids, amphoteric surfactants, sequestering agents, polymers, esters, antibacterial agents and water may be contained.

For example, in compositions for blending in waving agents, one to three kinds of ingredients selected from the group consisting of fats and oils, hydrocarbons, alkalis, amphoteric surfactants and polymers may be contained. In compositions for blending in finishing agents and in compositions for blending in thickening agents used on preparing hair treating agents, for example, silicones may be contained.

In compositions for blending in hair conditioners and in compositions for blending in waving agents, for example, acids and/or sequestering agents may be contained. In compositions for blending in thickening agents used on preparing hair treating agents, for example, esters may be contained. In compositions for blending in finishing agents, for example, antibacterial agents may be contained. In compositions for blending in compositions for blending in hair conditioners, in compositions for blending in waving agents and in compositions for blending in finishing agents, for example, water may be contained.

Examples of fats and oils include lanolin. Examples of hydrocarbons include liquid petrolatum. Examples of silicones include polyoxyethylene•methyl polysiloxane copolymer or methylphenyl polyethylene siloxane (degree of viscosity, e.g. 10~100 cs). Examples of alkalis include sodium hydroxide.

Examples of acids include one or two compounds selected from the group consisting of phosphoric acid, dibasic sodium phosphate and sorbic acid. Examples of amphoteric surfactant include lauryl dimethlaminoacetic acid betaine. Examples of sequestering agents include disodium edetate or hydroxyethane diphosphoric acid.

Examples of polymers include polyethylene glycol (average molecular weight, e.g. 300~500). Examples of esters include polyethylene (100~200 EO) glycol disterarate. Examples of antibacterial agents include phenoxyethanol.

In the formulations of the compositions for blending in hair treating agents of the present invention, when the respective contents of cationic surfactants and nonionic surfactants are B and C (wt %), B and C desirably satisfy the expressions of $0.5 \leq B \leq 30$, $0.1 \leq C \leq 95$ and $B+C \leq 100$.

For example, in a case of the compositions for blending in hair conditioners and the compositions for blending in waving agents, B and C may be $0.5 \leq B \leq = 30$, $1 \leq C \leq 95$ and $B+C \leq 100$.

In a case of compositions for blending in finishing agents, B and C may be $5 \leq B \leq 30$, $0.1 \leq C \leq 10$.

In a case of compositions for blending in thickening agents used on preparing hair treating agents, B and C may be $0.5 \leq B \leq 10$, $65 \leq C \leq 95$ and $B+C \leq 100$.

As the substantial method to prepare the compositions for blending in hair treating agents of this embodiment, following method may be exemplified. That is, cationic surfactants, nonionic surfactants and ingredients such as additives (If necessary) are mixed and stirred under heating (If necessary) until completely dissolved. The heating temperature is desirably lower than the decomposition temperature of the mixture, for example, lower than 95° C. The adding order of each ingredient is not limited.

In another preparation method of the compositions for blending in hair treating agents of this embodiment, for example, nonionic surfactants and other oiliness ingredients (e.g. fats and oils, hydrocarbons) are mixed and dissolved homogeneously under heating. This homogeneously dissolved material is added with stirring to heated water to prepare emulsion, and then this emulsion is cooled.

On the other hand, cationic surfactants and water are mixed with stirring under heating and dissolved homogeneously, and then cooled. Next, this homogeneously dissolved material is added with stirring to the above-mentioned emulsion, and then mixed homogeneously to prepare the compositions for blending in hair treating agents of this embodiment. The heating temperature is desirably lower than the decomposition temperature of the mixture, for example, lower than 95° C.

The hair treating agents of the present invention contain the above-mentioned compositions for blending in hair treating agents of the present invention. Hair conditioners, waving agents, finishing agents and thickening agents used on preparing hair treating agents are illustrated below as the hair treating agents.

The hair conditioners of the present invention contain above-mentioned compositions for blending in hair conditioners. One or more kinds of the compositions for blending in hair conditioners may be used.

Further, in the hair conditioners of the present invention, polymers and water may be contained as additives. Examples of polymers include hydroxyethyl cellulose (degree of viscosity of 1% aqueous solution, e.g. 500~5000 cps).

In the formulations of the hair conditioners of the present invention, the contents of the compositions for blending in hair conditioners are, for example, from 5 to 30 wt. %.

The preparing methods of the hair conditioners of the present invention are not limited. For example, the composition for blending in hair conditioner is heated to obtain homogeneously dissolved material. On the other hand, water and polymers are mixed and heated to prepare homogeneously dissolved material. To this homogeneously dissolved material, the aforementioned homogeneously dissolved material is added with stirring to be emulsified. After cooling, the hair conditioner of the present invention is prepared.

Waving agents of the present invention may be composed of No.1 agents and No.2 agents (In the present invention, both No.1 agents alone and No.2 agents alone are also included in the hair treating agents of the present invention).

No.1 agents of the waving agents of the present invention may contain reducing agents, alkaline agents and water besides the compositions for blending in waving agents of the present invention. Examples of the reducing agents include thioglycolic acid and cysteine or their salts [ammonium salt, MEA salt, hydrochloric acd salts etc.]. Examples of the alkaline agents include ammonia, amines (MEA, isopropanolamine, etc.), ammonium salts (ammonium bicarbonate etc.) and basic amino acid.

In formulations of No.1 agents of the waving agents of the present invention, the contents of the compositions for blending in waving agents may be, for example, 0.1~25 wt. %.

In No.2 agents of the waving agents of the present invention, oxidizing agents, surfactants, sequestering agents and water etc. may be contained besides the compositions for blending in waving agents of the present invention. Examples of the oxidizing agents include salts of bromic acid (e.g. sodium bromate) and hydrogen peroxide. Examples of the surfactants include lauryl trimethyl ammonium halide (lauryl trimethyl ammonum chloride, lauryl trimethyl ammonium bromide etc.). Examples of the sequestering agents include disodium edetate and 1-hydroxyethane-1, 1-diphosphonic acid.

In formulations of No.2 agents of the waving agents, the contents of the compositions for blending in waving agents may be, for example, 1~15 wt. %.

Conventional No.2 agents of the waving agents may be used instead of No.2 agents of the waving agents of the present invention. Examples of such conventional No.2 agents of the waving agents include the mixture prepared by dissolving oxidizing agents (e.g. sodium bromate) and surfactants (lauryl trimethyl ammonum chloride, lauryl trimethyl ammonium bromide etc.) homogeneously in water.

As the substantial method to prepare No.1 agents of the present waving agents, following method may be exemplified. That is, for example, the composition for blending in waving agent, that has been heated and dissolved homogeneously, is added to heated water, stirred and emulsified. Then, viscous liquid is prepared by cooling. Next, reducing agents and alkaline agents may be added to the viscous liquid at room temperature, and mixed homogeneously as stirring. The contents of the compositions for blending in waving agents in viscous liquids may be, for example, from 1 to 20 wt. %.

As another method to prepare No.1 agent of the present waving agent, following method may be exemplified. That is, for example, the composition for blending in waving agent, reducing agent, alkaline agent and water are added, and then mixed as stirring under heating, if necessary, to prepare No.1 agent of the present waving agent.

In No.2 agents of the waving agents of the present invention, for example, the composition for blending in waving agent, oxidizing agents and water are added, and then mixed as stirring under heating, if necessary, to prepare No.2 agent of the present waving agent.

The waving agents of the present invention contain at least one selected from the group consisting of No.1 agents of waving agents of the present invention and No.2 agents of waving agents of the present invention. For example, the waving agents of the present invention is one consisting of No.1 agents of waving agents of the present invention and No.2 agents of waving agents of the present invention, one consisting of No.1 agents of waving agents of the present invention and No.2 agents of waving agents except the above-mentioned ones, and another one consisting of No.1 agents of waving agents except the above-mentioned ones and No.2 agents of waving agents of the present invention.

As "No.1 agents of waving agents except the above-mentioned ones" and "No.2 agents of waving agents except the above-mentioned ones", the No.1 and No.2 agents, which are ordinary used in the conventional waving agents, may be exemplified respectively. Concrete examples of the No.2 agents of waving agents except the above-mentioned ones' include the mixture prepared, by dissolving oxidizing agents and surfactants homogeneously in water.

The finishing agents of the present invention contain the compositions for blending in finishing agents, and may further contain, if necessary, alcohols, preservatives and perfumes as additives.

Examples of alcohols include ethanol. Examples of preservatives include parabens.

In formulations of the finishing agents of the present invention, the contents of the compositions for blending in finishing agents may be, for example, 1~35 wt. %.

As the substantial methods to prepare the finishing agents of the present invention, following method may be exemplified. That is, for example, the compositions for blending in finishing agents, alcohols, preservatives, perfumes and water are added as stirring in order, and then mixed homogeneously under heating, if necessary, to prepare the finishing agents.

Thickening agents used on preparing hair treating agents of the present invention are such ones as may be blended to hair treating agents such as waving agents when hair treating agents are prepared and as can increase the viscosity of hair treating agents such as waving agents. Thickening agents used on preparing hair treating agents of the present invention contain the compositions for blending in thickening agents used on preparing hair treating agents of the present invention, and may further contain esters, glycols, preservatives and water.

Examples of esters include fatty esters such as cetyl octanoate. Examples of glycols include 1,3-butylene glycol. Examples of preservatives include parabens such as methyl parahydroxybenzoate.

In formulations of thickening agents used on preparing hair treating agents of the present invention, the compositions for blending in thickening agents used on preparing hair treating agents may be 40~80 wt. %.

As the substantial methods to prepare the thickening agents used on preparing hair treating agents of the present invention, following method may be exemplified. That is, for example, the compositions for blending in thickening agents used on preparing hair treating agents, esters, glycols and preservatives are dissolved homogeneously under heating, if necessary. Next, this homogeneously dissolved materials is added with stirring to water, and then mixed homogeneously to prepare the thickening agents used on preparing hair treating agents of the present invention.

EXAMPLE

Example of the First Embodiment

The first embodiment of the present invention is illustrated more concretely according to the following Examples.

(Preparation of the Composition for Blending in Hair Treating Agent)

Examples 1,18~23,25 and 26

The amount (kg) shown in Table 1~6 of each ingredient was heated to the temperature shown in Table 1, 3 or 5, and then mixed homogeneously with stirring. Thus, the composition for blending in hair treating agent (Examples 1,18~23, 25 and 26) of the present invention was prepared. The ingredients and contents (kg) are shown in Table 1~6.

Examples 2~7,9~11 and 13

Each ingredient except ingredient 38, 41,45 and 51 was heated to the temperature shown in Table 1 or 3, and then dissolved homogeneously. This homogeneously dissolved material was added with stirring to ingredient 51, which had been heated to the temperature shown in Table 1 or 3, and then emulsified. After the emulsion was cooled below 45° C., ingredient 38, 45 and 41 were added to the emulsion, and further ingredient 51 (add water) was added so as to adjust the total weight to be 100 kg. Thus, the composition for blending in hair treating agent of the present invention (Examples 2~7, 9~11 and 13) was prepared. Each numbers indicating ingredient, the ingredients and contents (kg) are shown in Table 1~4.

Example 8

Ingredient 3 (0.76 kg) was heated to 45~50° C. 0.38 kg of perfumes [trade name, "BOIS DE ROSE" (Meiji Koryo co.)] was added to this and dispersed homogeneously. Then, ingredient 51 (3.98 kg) was added with stirring, and then mixed homogeneously to prepare an agent for solbilizing perfumes.

On the other hand, ingredient 5 (2.99 kg) and ingredient 51 (5.3 kg) were heated to 70~90° C., and then mixed homogeneously. After this homogeneous mixture was cooled below 40° C., the cooled mixture was added to 86.34 kg of the composition for blending in a hair treating agent (Example 11), and stirred to prepare homogeneous composition. The aforementioned agent for solbilizing perfume and above-mentioned homogeneous composition are mixed with stirring. Thus, the composition for blending in hair treating agent of the present invention was prepared. Each number indicating ingredient, the ingredients and contents (kg) are shown in Table 1 and 2.

Examples 12

Each ingredient 1, 39, 40 and 51 (36.42 kg) were heated to the temperature shown in Table 3, and then mixed homogeneously. After cooled below 40° C., mixture with ingredient 41 and 51 and ingredient 20 were added in order to the cooled mixture, and then mixed homogeneously with stirring. Thus, the composition for blending in hair treating agent of the present invention was prepared. Each number indicating ingredient, the ingredients and contents (kg) are shown in Table 3 and 4.

Example 14

Ingredient 1 was added to ingredient 51 (41.46 kg), which had been heated to the temperature shown in Table 3, and dissolved. To this, ingredient 39 and 40 were added, and cooled with stirring homogeneously below 45° C. Next, ingredient 41 was added, and further ingredient 51 (add water) was added so as to adjust the total weight to be 100 kg, and then mixed homogeneously with stirring. Thus, the composition for blending in hair treating agent of the present invention was prepared. Each number indicating ingredient, the ingredients and contents (kg) are shown in Table 3 and 4.

Examples 15, 16

Each ingredient except ingredient 51 was heated to the temperature shown in Table 3, and then dissolved homogeneously. Ingredient 51, which had been heated to the temperature shown in Table 3, was added with stirring to this homogeneously dissolved material. After cooled below 45° C., ingredient 51 (add water) was added so as to adjust the total weight to be 100 kg, and then mixed homogeneously with stirring. Thus, the composition for blending in hair treating agent of the present invention was prepared. Each number indicating ingredient, the ingredients and contents (kg) are shown in Table 3 and 4.

Examples 17

Each ingredient 12, 19, 33 and 50 was mixed and heated to the temperature shown in Table 3 to be dissolved homogeneously. After cooled below 50° C., ingredient 51 (49.21 kg), 47 and 42 were added in order, and finally ingredient 51 (add water) was added so as to adjust the total weight to be 100 kg, and then mixed homogeneously with stirring. Thus, the composition for blending in hair treating agent of the present invention was prepared. Each number indicating ingredient, the ingredients and contents (kg) are shown in Table 3 and 4.

Examples 24

Ingredient 21 was dissolved in ingredient 51(20 kg), which had been heated to 80~90° C., to prepare mixture I. Ingredient 22 was dissolved in ingredient 51(30 kg), which had been heated to 80~90° C., to prepare mixture II. Ingredient 19, 49 and 50 were heated to 80~90° C., and then ingredient 51 was added to prepare mixture III.

Next, each ingredient I, II and III were added in order, and then mixed homogeneously with stirring. Thus, the composition for blending in hair treating agent of the present invention was prepared. Each number indicating ingredient, the ingredients and contents (kg) are shown in Table 5 and 6.

Examples 27

Each ingredient 6, 13, 24 (4 kg) and 25 was mixed and heated to the temperature shown in Table 5 to prepare homogeneously dissolved material I. On the other hand, ingredient 24 and 48 were mixed and heated to the temperature shown in Table 5 to prepare homogeneously dissolved material II. To homogeneously dissolved material I, homogeneously dissolved material II was added, and then mixed homogeneously with stirring. Thus, the composition for blending in hair treating agent of the present invention was prepared. Each number indicating ingredient, the ingredients and contents (kg) are shown in Table 5 and 6.

Examples 28 and 29

Each ingredient except ingredient 18 was mixed homogeneously with stirring. And then, to this homogeneous mixture, ingredient 18 was added with stirring, and then dispersed homogeneously. Thus, the composition for blending in hair treating agent (Examples 28 and 29) of the present invention was prepared. Each number indicating ingredient, the ingredients and contents (kg) are shown in Table 5 and 6.

TABLE 1

| | | Example | | | | | | | | | |
|---|---|---|---|---|---|---|---|---|---|---|---|
| | | 1 | 2 | 3 | 4 | 5 | 6 | 7 | 8 | 9 | 10 |
| | | | | | | heating temperature (° C.) | | | | | |
| | ingredient (kg) | 80 | 93~95 | 80 | 90 | 93~95 | 86~90 | 85 | 45~50 | 90 | 90 |
| 1 | polyoxyethylene lauryl ether | — | — | — | — | — | — | — | — | — | — |
| 2 | polyoxyethylene cetyl ether | — | — | — | — | — | — | — | — | — | — |
| 3 | polyoxyethylene oleyl ether | 32[1] | 7[2] | 1[3] | 7[4] | 8[5] | 5[6] | 6[7] | 8[8] | 9[9] | 8[10] |
| 4 | polyoxyethylene nonylphenyl ether | — | — | — | — | — | 1[11] | — | — | — | — |

TABLE 1-continued

| | | Example | | | | | | | | | |
|---|---|---|---|---|---|---|---|---|---|---|---|
| | | 1 | 2 | 3 | 4 | 5 | 6 | 7 | 8 | 9 | 10 |
| | | heating temperature (° C.) | | | | | | | | | |
| | ingredient (kg) | 80 | 93~95 | 80 | 90 | 93~95 | 86~90 | 85 | 45~50 | 90 | 90 |
| 5 | polyoxyethylene lanolin | — | — | — | — | — | — | — | 3[12] | — | 3[13] |
| 6 | polyoxyethylene hydrogenated castor oil | — | — | — | — | — | — | — | — | — | — |
| 7 | sorbitan monostearate | — | — | — | — | — | — | — | — | — | — |
| 8 | sorbitan monooleate | — | 3 | 4 | 4 | 3 | 2 | 4 | — | — | — |
| 9 | sorbitan sesquioleate | — | — | — | — | — | 2 | — | — | — | — |
| 10 | polyoxyethylene sorbitan monooleate | — | — | 9[14] | — | — | — | — | — | — | — |
| 11 | oleic acid diethanolamide | — | — | — | — | — | — | — | — | — | — |
| 12 | polyoxyethylene polyoxypropylene glycol | — | — | — | — | — | — | — | — | — | — |
| 13 | decamethyl cyclopentasiloxane | — | — | — | — | — | — | — | — | — | — |
| 14 | methyl polysiloxane | — | — | — | — | — | — | — | — | — | — |
| 15 | methylphenyl polysiloxane | — | 16[15] | — | — | — | — | — | — | — | — |
| 16 | dimethylsiloxane · methylstearoxysiloxane copolymer | — | 4[16] | — | — | — | — | — | — | — | — |
| 17 | aminoethylaminopropylsiloxane · dimethylsiloxane copolymer | — | — | — | — | — | — | — | — | — | — |
| 18 | carboxyvinylpolymer | — | — | — | — | — | — | — | — | — | — |
| 19 | polyethylene glycol | — | — | — | — | — | — | — | — | — | — |
| 20 | styrene polymer emulsion | — | — | — | — | — | — | — | — | — | — |
| 21 | polyvinylpyrrolidone | — | — | — | — | — | — | — | — | — | — |
| 22 | hydroxyethyl cellulose | — | — | — | — | — | — | — | — | — | — |

[1]–[16] in Table 1 indicate,
[1] 16 kg (4 EO) + 8 kg (8 EO) + 8 kg(13 EO),
[2] 5.5 kg (20 EO) + 1.5 kg (30 EO),
[3] 13 EO,
[4] 0.58 kg (4 EO) + 6.04 kg (13 EO) + 0.38 kg (30 EO),
[5] 1.33 kg (4 EO) + 3.56 kg (13 EO) + 3.11 kg (30 EO),
[6] 13 EO,
[7] 13 EO,
[8] 13 EO,
[9] 7.5 kg (7 EO) + 1.5 kg (20 EO),
[10] 4 kg (8 EO) + 4 kg (13 EO),
[11] 6 EO,
[12] 70 EO,
[13] 70 EO,
[14] 20 EO,
[15] 14 cs,
[16] softening point; 40~50° C.

TABLE 2

| | | Example | | | | | | | | | |
|---|---|---|---|---|---|---|---|---|---|---|---|
| | ingredient (kg) | 1 | 2 | 3 | 4 | 5 | 6 | 7 | 8 | 9 | 10 |
| 23 | olive oil | — | — | — | — | — | — | — | — | — | — |
| 24 | safflower oil | — | — | — | — | — | — | — | — | — | — |
| 25 | castor oil | — | — | — | — | — | — | — | — | — | — |
| 26 | lanolin | — | — | — | — | — | — | — | 3 | 6 | 3 |
| 27 | hydrogenated oil | 22[1] | — | — | — | — | — | — | — | — | — |
| 28 | mink oil | — | — | — | 10 | — | — | — | — | — | — |
| 29 | liquid petrolatum | — | 10 | 24 | 20 | 20 | 20 | 28 | 18 | 14 | 19 |
| 30 | light liquid isoparaffin | 11 | — | — | — | — | — | — | — | — | — |
| 31 | chlorinated paraffin | — | — | 16 | — | 10 | 10 | 12 | 6 | — | 6 |
| 32 | microcrystalline wax | 35 | — | — | — | — | — | — | — | — | — |
| 33 | ammonium polyoxyethylene lauryl ether sulfate | — | — | — | — | — | — | — | — | — | — |
| 34 | triethanolamine polyoxyethylene lauryl ether sulfate | — | — | — | — | — | — | — | — | — | — |
| 35 | lauric acid | — | — | — | — | — | — | — | — | — | — |
| 36 | stearic acid | — | — | — | — | — | — | — | — | — | — |
| 37 | oleic acids | — | — | — | 1 | 1 | — | — | 0.4 | — | 0.5 |
| 38 | sorbic acid | — | 0.26 | 0.26 | 0.26 | 0.26 | 0.36 | 0.26 | 0.23 | 0.26 | 0.23 |
| 39 | 2-alkyl-N-carboxymethyl, N-hydroxyethyl imidazolinium betaine | — | — | — | — | — | — | — | — | — | — |
| 40 | cocoyl amide propyldimethyl glycine | — | — | — | — | — | — | — | — | — | — |
| 41 | phosphoric acid[2] | — | 0.15 | 0.05 | 0.05 | 0.04 | 0.28 | 0.04 | 0.1 | 0.05 | 0.1 |
| 42 | dibasic sodium phosphate | — | — | — | — | — | — | — | — | — | — |
| 43 | monobasic sodium phosphate | | | | | | | | | | |

TABLE 2-continued

|    | ingredient (kg) | 1 | 2 | 3 | 4 | 5 | 6 | 7 | 8 | 9 | 10 |
|---|---|---|---|---|---|---|---|---|---|---|---|
| 44 | triethanolamine | — | — | — | — | — | — | — | — | — | — |
| 45 | sodium hydroxide | — | 0.1 | 0.11 | 0.11 | 0.11 | 0.14 | 0.11 | 0.1 | 0.11 | 0.1 |
| 46 | 1-hydroxyethane-1,1-diphosphonic acid | — | — | — | — | — | — | — | — | — | — |
| 47 | disodium edetate | — | — | — | — | — | — | — | — | — | — |
| 48 | dibutylhydroxytoluene | — | — | — | — | — | — | — | — | — | — |
| 49 | propyl parahydroxybenzoate | — | — | — | — | — | — | — | — | — | — |
| 50 | methyl parahydroxybenzoate | — | — | — | — | — | — | — | — | — | — |
| 51 | water | — | 59.49 | 45.58 | 57.58 | 57.59 | 59.22 | 49.59 | 60.07 | 70.58 | 60.07 |

[1] and [2] in Table 2 indicate,
[1] hydrogenated palm oil fatty acid triglyceride:hydrogenated tallow fatty acid triglyceride = about 1:1 (weight ratio),
[2] Content; 85 wt. %.

TABLE 3

|    | ingredient (kg) | 11 | 12 | 13 | 14 | 15 | 16 | 17 | 18 | 19 | 20 |
|---|---|---|---|---|---|---|---|---|---|---|---|
|    | heating temperature (° C.) | 85 | 70~80 | 80~90 | 70~80 | 80 | 80 | 80~85 | — | — | — |
| 1 | polyoxyethylene lauryl ether | — | 0.4[1] | — | 0.5[2] | — | — | — | — | — | — |
| 2 | polyoxyethylene cetyl ether | — | — | — | — | — | — | — | — | — | — |
| 3 | polyoxyethylene oleyl ether | 9[3] | — | 18[4] | — | — | — | — | — | — | — |
| 4 | polyoxyethylene nonylphenyl ether | — | — | — | — | — | — | — | — | — | — |
| 5 | polyoxyethylene lanolin | — | — | — | — | — | — | — | — | — | — |
| 6 | polyoxyethylene hydrogenated castor oil | — | — | — | — | — | — | — | — | — | — |
| 7 | sorbitan monostearate | — | — | — | — | — | — | — | — | — | — |
| 8 | sorbitan monooleate | — | — | — | — | — | — | — | — | — | — |
| 9 | sorbitan sesquioleate | — | — | — | — | — | — | — | — | — | — |
| 10 | polyoxyethylene sorbitan monooleate | — | — | — | — | — | — | — | — | — | — |
| 11 | oleic acid diethanolamide | — | — | — | — | 5 | 1 | — | — | — | — |
| 12 | polyoxyethylene polyoxypropylene glycol | — | — | — | — | — | — | 8[5] | — | — | — |
| 13 | decamethyl cyclopentasiloxane | — | — | — | — | — | — | — | 89 | 44.5 | — |
| 14 | methyl polysiloxane | — | — | — | — | — | — | — | 11[6] | 5.5[7] | 100[8] |
| 15 | methylphenyl polysiloxane | — | — | — | — | — | — | — | — | 50 | — |
| 16 | dimethylsiloxane · methylstearoxysiloxane copolymer | — | — | — | — | — | — | — | — | — | — |
| 17 | aminoethylaminopropylsiloxane · dimethylsiloxane copolymer | — | — | — | — | — | — | — | — | — | — |
| 18 | carboxyvinylpolymer | — | — | — | — | — | — | — | — | — | — |
| 19 | polyethylene glycol | — | — | — | — | — | — | 2[9] | — | — | — |
| 20 | styrene polymer emulsion | — | 13 | — | — | — | — | — | — | — | — |
| 21 | polyvinylpyrrolidone | — | — | — | — | — | — | — | — | — | — |
| 22 | hydroxyethyl cellulose | — | — | — | — | — | — | — | — | — | — |

[1]-[9] in Table 3 indicate,
[1] 23 EO,
[2] 23 EO,
[3] 4.5 kg (6 EO) + 4.5 kg (13 EO),
[4] 12 kg (13 EO) + 6 kg (50 EO),
[5] 30 EO, 55 PO,
[6] 9 kg (average molecular weight, more than 650) + 2 kg (3000 cs),
[7] 3.6 kg (average molecular weight, more than 650) + 0.9 kg (20 cs) + 1 kg (3000 cs),
[8] 50 kg (20 cs) + 20 kg (3000 cs),
[9] Average molecular weight; 6000.

TABLE 4

|    | ingredient (kg) | 11 | 12 | 13 | 14 | 15 | 16 | 17 | 18 | 19 | 20 |
|---|---|---|---|---|---|---|---|---|---|---|---|
| 23 | olive oil | — | — | — | — | — | — | — | — | — | — |
| 24 | safflower oil | — | — | — | — | — | — | — | — | — | — |
| 25 | castor oil | — | — | — | — | — | — | — | — | — | — |
| 26 | lanolin | 3 | — | — | — | — | — | — | — | — | — |
| 27 | hydrogenated oil | — | — | — | — | — | — | — | — | — | — |
| 28 | mink oil | — | — | — | — | — | — | — | — | — | — |
| 29 | liquid petrolatum | 20 | — | — | — | — | — | — | — | — | — |

TABLE 4-continued

| | ingredient (kg) | Example | | | | | | | | | |
|---|---|---|---|---|---|---|---|---|---|---|---|
| | | 11 | 12 | 13 | 14 | 15 | 16 | 17 | 18 | 19 | 20 |
| 30 | light liquid isoparaffin | — | — | — | — | — | — | — | — | — | — |
| 31 | chlorinated paraffin | 7 | — | — | — | — | — | — | — | — | — |
| 32 | microcrystalline wax | — | — | — | — | — | — | — | — | — | — |
| 33 | ammonium polyoxyethylene lauryl ether sulfate | — | — | — | — | — | — | 40[3)] | — | — | — |
| 34 | triethanolamine polyoxyethylene lauryl ether sulfate | — | — | — | — | 47[1)] | 45[2)] | — | — | — | — |
| 35 | lauric acid | — | — | — | — | 2 | 1.5 | — | — | — | — |
| 36 | stearic acid | — | — | — | — | — | — | — | — | — | — |
| 37 | oleic acids | 1 | — | — | — | — | — | — | — | — | — |
| 38 | sorbic acid | 0.26 | — | 0.26 | — | — | — | — | — | — | — |
| 39 | 2-alkyl-N-carboxymethyl, N-hydroxyethyl imidazolinium betaine[4)] | — | 11 | — | 13 | — | — | — | — | — | — |
| 40 | cocoyl amide propyldimethyl glycine[5)] | — | 17 | — | 17 | 4 | 11 | — | — | — | — |
| 41 | phosphoric acid[6)] | 0.05 | 0.2 | 0.04 | 0.2 | — | — | — | — | — | — |
| 42 | dibasic sodium phosphate | — | — | — | — | — | — | 0.2 | — | — | — |
| 43 | monobasic sodium phosphate | — | — | — | — | — | — | — | — | — | — |
| 44 | triethanolamine | — | — | — | — | 7 | 4.5 | — | — | — | — |
| 45 | sodium hydroxide | 0.11 | — | 0.11 | — | — | — | — | — | — | — |
| 46 | 1-hydroxyethane-1,1-diphosphonic acid[7)] | — | — | — | — | 1.5 | 1.5 | — | — | — | — |
| 47 | disodium edetate | — | — | — | — | — | — | 0.1 | — | — | — |
| 48 | dibutylhydroxytoluene | — | — | — | — | — | — | — | — | — | — |
| 49 | propyl parahydroxybenzoate | — | — | — | — | — | — | — | — | — | — |
| 50 | methyl parahydroxybenzoate | — | — | — | — | 0.05 | 0.05 | 0.2 | — | — | — |
| 51 | water | 59.58 | 58.4 | 81.59 | 69.3 | 33.45 | 35.45 | 49.5 | — | — | — |

[1)]–[7)] in Table 4 indicate,
[1)] 3 EO, Content 36 wt. %,
[2)] 3 EO, Content 36 wt. %,
[3)] 2 EO, Content 27 wt. %,
[4)] Content 50 wt. %,
[5)] Content 30 wt. %,
[6)] Content 85 wt. %,
[7)] Content 60 wt. %.

TABLE 5

| | ingredient (kg) | Example | | | | | | | | |
|---|---|---|---|---|---|---|---|---|---|---|
| | | 21 | 22 | 23 | 24 | 25 | 26 | 27 | 28 | 29 |
| | | | | | heating temperature (° C.) | | | | | |
| | | — | — | — | 80~90 | 80~90 | 70~80 | 50 | — | — |
| 1 | polyoxyethylene lauryl ether | — | — | — | — | — | — | — | — | — |
| 2 | polyoxyethylene cetyl ether | — | — | — | — | — | 10[1)] | — | — | — |
| 3 | polyoxyethylene oleyl ether | — | — | — | — | — | — | — | — | — |
| 4 | polyoxyethylene nonylphenyl ether | — | — | — | — | — | — | — | — | — |
| 5 | polyoxyethylene lanolin | — | — | — | — | — | — | — | — | — |
| 6 | polyoxyethylene hydrogenated castor oil | — | — | — | — | — | — | 10[2)] | — | — |
| 7 | sorbitan monostearate | — | — | — | — | — | — | 4 | — | — |
| 8 | sorbitan monooleate | — | — | — | — | — | — | — | — | — |
| 9 | sorbitan sesquioleate | — | — | — | — | — | — | — | — | — |
| 10 | polyoxyethylene sorbitan monooleate | — | — | — | — | — | — | — | — | — |
| 11 | oleic acid diethanolamide | — | — | — | — | — | — | — | — | — |
| 12 | polyoxyethylene polyoxypropylene glycol | — | — | — | — | — | — | — | — | — |
| 13 | decamethyl cyclopentasiloxane | 87 | — | 56 | — | — | — | 5 | — | — |
| 14 | methyl polysiloxane | 13[3)] | 85[4)] | 44[5)] | — | — | — | — | — | — |
| 15 | methylphenyl polysiloxane | — | — | — | — | — | — | — | — | — |
| 16 | dimethylsiloxane · methylstearoxysiloxane copolymer | — | — | — | — | — | — | — | — | — |
| 17 | aminoethylaminopropylsiloxane · dimethylsiloxane copolymer | — | 15 | — | — | — | — | — | — | — |
| 18 | carboxyvinylpolymer | — | — | — | — | — | — | — | 5[6)] | 5[7)] |
| 19 | polyethylene glycol | — | — | — | 20[8)] | 3[9)] | — | — | — | — |

TABLE 5-continued

| | Example | | | | | | | | |
|---|---|---|---|---|---|---|---|---|---|
| | 21 | 22 | 23 | 24 | 25 | 26 | 27 | 28 | 29 |
| | | | | heating temperature (° C.) | | | | | |
| ingredient (kg) | — | — | — | 80~90 | 80~90 | 70~80 | 50 | — | — |
| 20 styrene polymer emulsion | — | — | — | — | — | — | — | — | — |
| 21 polyvinylpyrrolidone | — | — | — | 1.2[10) | — | — | — | — | — |
| 22 hydroxyethyl cellulose | — | — | — | 0.3[11) | — | — | — | — | — |

[1)–11) in Table 5 indicate,

[1) 7 EO,

[2) 10 EO,

[3) 9 kg (average molecular weight, more than 650) + 4 kg (3000 cs),

[4) 12.75 kg (average molecular weight, more than 650) + 72.25 kg (20 cs),

[5) 8 kg (100 cs) + 16 kg (3000 cs) + 20 kg (1 million cs),

[6) Average molecular weight; 1250000,

[7) Average molecular weight; 4 million,

[8) 17 kg (average molecular weight, 4000) + 3 kg (average molecular weight, 6000),

[9) Average molecular weight; 4 million,

[10) Average molecular weight; 360000,

[11) Degree of viscosity; 5000~10000 cps (2% aqueous solution).

TABLE 6

| | | Example | | | | | | | | |
|---|---|---|---|---|---|---|---|---|---|---|
| | ingredient (kg) | 21 | 22 | 23 | 24 | 25 | 26 | 27 | 28 | 29 |
| 23 | olive oil | — | — | — | — | — | 63 | — | — | — |
| 24 | safflower oil | — | — | — | — | — | — | 5 | — | — |
| 25 | castor oil | — | — | — | — | — | 6 | 79.95 | — | — |
| 26 | lanolin | — | — | — | — | — | — | — | — | — |
| 27 | hydrogenated oil | — | — | — | — | — | 2[1) | — | — | — |
| 28 | mink oil | — | — | — | — | — | — | — | — | — |
| 29 | liquid petrolatum | — | — | — | — | — | — | — | — | — |
| 30 | light liquid isoparaffin | — | — | — | — | — | 6 | — | — | — |
| 31 | chlorinated paraffin | — | — | — | — | — | — | — | — | — |
| 32 | microcrystalline wax | — | — | — | — | — | — | — | — | — |
| 33 | ammonium polyoxyethylene lauryl ether sulfate | — | — | — | — | — | — | — | — | — |
| 34 | triethanolamine polyoxyethylene lauryl ether sulfate | — | — | — | — | — | — | — | — | — |
| 35 | lauric acid | — | — | — | — | — | — | — | — | — |
| 36 | stearic acid | — | — | — | — | — | 9 | — | — | — |
| 37 | oleic acids | — | — | — | — | — | — | — | — | — |
| 38 | sorbic acid | — | — | — | — | — | — | — | — | — |
| 39 | 2-alkyl-N-carboxymethyl, N-hydroxyethyl imidazolinium betaine | — | — | — | — | — | — | — | — | — |
| 40 | cocoyl amide propyldimethyl glycine | — | — | — | — | — | — | — | — | — |
| 41 | phosphoric acid[2) | — | — | — | — | — | — | — | 3 | 3 |
| 42 | dibasic sodium phosphate | — | — | — | — | — | — | — | — | — |
| 43 | monobasic sodium phosphate | — | — | — | — | — | — | — | 0.1 | — |
| 44 | triethanolamine | — | — | — | — | — | — | — | — | — |
| 45 | sodium hydroxide | — | — | — | — | — | — | — | — | — |
| 46 | 1-hydroxyethane-1,1-diphosphonic acid[3) | — | — | — | — | — | — | — | 0.1 | 0.1 |
| 47 | disodium edetate | — | — | — | — | — | — | — | — | — |
| 48 | dibutylhydroxytoluene | — | — | — | — | — | — | 0.05 | — | — |
| 49 | propyl parahydroxybenzoate | — | — | — | 0.1 | — | — | — | — | — |
| 50 | methyl parahydroxybenzoate | — | — | — | 0.1 | 0.1 | — | — | — | — |
| 51 | water | — | — | — | 78.3 | 96.9 | — | — | 91.8 | 91.9 |

[1)–3) in Table 6 indicate,

[1) hydrogenated castor oil,

[2) Content, 85 wt. %,

[3) Content, 60 wt. %.

(Preparation of Hair Conditioner)

Examples 30 and 31

After the composition for blending in hair conditioner (Example 20 or 22) and additive composition were mixed, heated to 80~85° C., and dispersed homogeneously, water, which had been heated to 80~85° C., was added, and then mixed homogeneously with stirring. Thus, the hair conditioner (Examples 30 and 31) of the present invention was prepared. The ingredients and contents (kg) are shown in Table 7.

TABLE 7

| | Example | |
|---|---|---|
| ingredient(kg) | 30 | 31 |
| composition for blending in hair conditioner | Example 20 5 | Example 22 5 |
| additive composition[1] | 20 | 20 |
| water | remaining volume | remaining volume |
| total weight | 100 | 100 |

[1] in Table 7 indicates;
[1] Ingredient (wt. %); cetanol (49), 60 wt. % of stearyl trimethyl ammonium chloride (15), 80 wt. % of behenyl trimethyl ammonium chloride (8), conc. glycerin (28).

(Preparation of Oxidizing Hair Coloring Agent)

Example 32

Preparation of No.1 Agent of Oxidizing Hair Coloring Agent

Dye intermediates (mixture with resorcinol, p-phenylene diamine, m-aminophenol and p-aminophenol) and water were mixed and heated to 80° C. to prepare aqueous solution. To this aqueous solution, the composition for blending in hair coloring was added and then mixed homogeneously with stirring. After cooled to room temperature, mixture with monoethanolamine (MEA) and strong ammonia solution was added, and then mixed homogeneously with stirring. Thus, No.1 agent of oxidizing hair coloring agent of the present invention was prepared. The ingredients and contents (kg) are shown in Table 8.

Preparation of No.2 Agent of Oxidizing Hair Coloring Agent

Each ingredient shown in Table 8 was mixed homogeneously with stirring. Thus, No.2 agent of oxidizing hair coloring agent of the present invention was prepared. The ingredients and contents (kg) are shown in Table 8.

(Preparation of Decolorizing Agent)

Example 33

Preparation of No. 1 Agent of Decolorizing Agent

No. 1 agent of decolorizing agent of the present invention was prepared in the same manner as Example 32 excepted that dye intermediates was not used. The ingredients and contents (kg) are shown in Table 8.

Preparation of No.2 Agent of Decolorizing Agent

No. 2 agent of decolorizing agent of the present invention was prepared in the same manner as Example 32. The ingredients and contents (kg) are shown in Table 8.

TABLE 8

| | Example | |
|---|---|---|
| ingredient(kg) | 32 | 33 |
| No. 1 agent | | |
| composition for blending in hair coloring | Example 29 40 | Example 29 40 |
| 80% MEA | 2.5 | 2.5 |
| strong ammonia solution | proper amount | proper amount |
| dye intermediate | proper amount | — |
| water | remaining volume | remaining volume |
| total weight | 100 | 100 |
| No. 2 agent | | |
| composition for blending in hair coloring | Example 4 2 | Example 4 2 |
| 60% hydroxyethane diphosphonic acid | 0.17 | 0.17 |
| dibasic sodium phosphate | 0.26 | 0.26 |
| 35% hydrogen peroxide solution | 16.9 | 16.9 |
| water | remaining volume | remaining volume |
| total weight | 100 | 100 |

(Preparation of Waving Agent)

Example 34

Preparation of No.1 Agent of Waving Agent

To one composition for blending in waving agent (Example 28), water, triethanolamine, mixture with ATG and strong ammonia aqueous solution and the other composition for blending in waving agent (Example 4) were added in order with stirring, and then mixed homogeneously. Thus, No.1 agent of waving agents of the present invention was prepared. The ingredients and contents (kg) are shown in Table 9.

Preparation of No.2 Agent of Waving Agent

No.2 agent of waving agent of the present invention was prepared in the same manner as following Examples 40~42. The ingredients and contents (kg) are shown in Table 9.

Example 35~38

Preparation of No.1 Agent of Waving Agent

To one composition for blending in waving agent (Example 29), water, monoethanolamine, the other composition for blending in waving agent (Example 4, 14, 16) or additive composition, ATG and strong ammonia aqueous solution were added in order with stirring, and then mixed homogeneously. Thus, No.1 agent of waving agents of the present invention was prepared. The ingredients and contents (kg) are shown in Table 9.

Preparation of No.2 Agent of Waving Agent

To one composition for blending in waving agent (Example 29), water, sodium hydroxide, the other composition for blending in waving agent (Example 4, 14, 16) or additive composition, sodium bromate and "KATHON CG" were added in order with stirring, and then mixed homogeneously. Thus, No.2 agent of waving agents of the present invention was prepared. The ingredients and contents (kg) are shown in Table 9.

Example 39

Preparation of No.1 Agent of Waving Agent

To one composition for blending in waving agent (Example 29), water, the other composition for blending in waving agent (Example 18), monoethanolamine, ATG and strong ammonia aqueous solution were added in order with stirring, and then mixed homogeneously. Thus, No.1 agent of waving agent of the present invention was prepared. The ingredients and contents (kg) are shown in Table 9.

Preparation of No.2 Agent of Waving Agent

To one composition for blending in waving agent (Example 29), water, the other composition for blending in waving agent (Example 18), sodium hydroxide, sodium bromate and "KATHON CG" were added in order with stirring, and then mixed homogeneously. Thus, No.2 agent of waving agent of the present invention was prepared. The ingredients and contents (kg) are shown in Table 9.

Example 40~45

Preparation of No.1 Agent of Waving Agent

Each ingredient shown in Table 9 was mixed homogeneously with stirring. Thus, No.1 agent of waving agent of the present invention was prepared. The ingredients and contents (kg) are shown in Table 9.

Preparation of No.2 Agent of Waving Agent

Each ingredient shown in Table 9 was mixed homogeneously with stirring. Thus, No.2 agent of waving agent of the present invention was prepared. The ingredients and contents (kg) are shown in Table 9.

TABLE 9

| ingredient(kg) | Example 34 | Example 35 | Example 36 | Example 37 | Example 38 | Example 39 |
|---|---|---|---|---|---|---|
| No. 1 agent | | | | | | |
| composition for blending in waving agent | Example 28 13 / Example 4 2 | Example 29 50 / Example 4 2 | Example 29 50 / Example 14 5 | Example 29 50 / Example 16 5 | Example 29 50 | Example 29 50 / Example 18 1 |
| additive composition | — | — | — | — | proper amount[1] | — |
| 50% ATG | 14 | 10 | 10 | 10 | 10 | 10 |
| alkaline agent | 3[2] | proper amount | proper amount | proper amount | proper amount | proper amount |
| 20% monoethanolamine | — | 12.5 | 12.5 | 12.5 | 12.5 | 12.5 |
| triethanolamine | 2.2 | — | — | — | — | — |
| water | remaining volume | remaining volume | remaining volume | remaining volume | remaining volume | remaining volume |
| total weight | 100 | 100 | 100 | 100 | 100 | 100 |
| No. 2 agent | | | | | | |
| composition for blending in waving agent | Example 5 2 | Example 29 50 / Example 4 | Example 29 50 / Example 14 | Example 29 50 / Example 16 | Example 29 50 | Example 29 50 / Example 18 1 |
| additive composition | — | — | — | — | proper amount[1] | — |
| sodium bromate | 8 | 24[3] | 24[3] | 24[3] | 24[3] | 24[3] |
| 20% sodium hydroxide | — | 11.8 | 11.8 | 11.8 | 11.8 | 11.8 |
| KATHON CG[4] | — | 0.06 | 0.06 | 0.06 | 0.06 | 0.06 |
| water | remaining volume | remaining volume | remaining volume | remaining volume | remaining volume | remaining volume |
| total weight | 100 | 100 | 100 | 100 | 100 | 100 |

| ingredient(kg) | Example 40 | Example 41 | Example 42 | Example 43 | Example 44 | Example 45 |
|---|---|---|---|---|---|---|
| No. 1 agent | | | | | | |
| composition for blending in waving agent | Example 4 2 | Example 6 2 | Example 8 2 | Example 12 5 | Example 14 5 | Example 16 5 |
| additive composition | — | — | — | — | — | — |
| 50% ATG | 13 | 13 | 13 | 13 | 13 | 13 |
| alkaline agent | proper amount[2] | proper amount[2] | proper amount[2] | proper amount[2] | proper amount[2] | proper amount[2] |
| 20% monoethanolamine | — | — | — | — | — | — |
| triethanolamine | — | — | — | — | — | — |
| water | remaining volume | remaining volume | remaining volume | remaining volume | remaining volume | remaining volume |
| total weight | 100 | 100 | 100 | 100 | 100 | 100 |

TABLE 9-continued

No. 2 agent

| composition for blending in waving agent | Example 5 2 | Example 5 2 | Example 5 2 | Example 17 5 | Example 17 5 | Example 17 5 |
|---|---|---|---|---|---|---|
| additive composition | — | — | — | — | — | — |
| sodium bromate | 8 | 8 | 8 | 8 | 8 | 8 |
| 20% sodium hydroxide | — | — | — | — | — | — |
| KATHON CG[4] | — | — | — | — | — | — |
| water | remaining volume | remaining volume | remaining volume | remaining volume | remaining volume | remaining volume |
| total weight | 100 | 100 | 100 | 100 | 100 | 100 |

[1]–[4] in Table 9 indicates;
[1]Ingredient (wt. %); polyoxyethylene (25 EO) lauryl ether (1), polyoxyethylene lanolin (1), 2-alkyl-N-carboxymethyl-N-hydroxyethyl imidazolinium betaine (15), triethanolamine polyoxyethylene lauryl ether sulfate (54), 1-hydroxyethane-1,1-diphosphonic acid (2), triethanolamine (2.1), isopropanol (3), water (21.9).
[2]strong ammonia aqueous solution,
[3]Content 25 wt. %,
[4]preservative, Rohm And Haas Japan co.

(Preparation of Finishing Agent)

Example 46

Potassium hydroxide, 70 kg of water and polyoxyethylene distearate was heated to 80~85° C., and then stirred to prepare aqueous solution. On the other hand, the composition for blending in a finishing agent (Example 1), parabens and remaining oiliness ingredients were heated to 80~85° C., and then stirred to prepare homogeneous mixture. This homogeneous mixture was added to the aforementioned aqueous solution, and emulsified with stirring. After this emulsion was cooled to 50° C., water (add water) was added so as to adjust the total weight to be 100 kg, and then mixed homogeneously. Thus, finishing agent of the present invention was prepared. The ingredients and contents (kg) are shown in Table 10.

Example 47 and 48

After each ingredient except water was mixed homogeneously with stirring, water was added and emulsified. Thus, finishing agent of the present invention was prepared. The ingredients and contents (kg) are shown in Table 10.

Example 49 and 50

Each ingredient shown in Table 10 was mixed with stirring to be dissolved homogeneously. Thus, finishing agent of the present invention was prepared. The ingredients and contents (kg) are shown in Table 10.

Example 51

The composition for blending in a finishing agent (Example 29), water, propylene glycol and Blue No.1 aqueous solution were mixed and stirred to prepare homogeneous mixture. To this homogeneous mixture, mixture with parabens and ethanol, potassium hydroxide and decamethyl cyclopentasiloxane were added in order, and then mixed homogeneously with stirring. Thus, the finishing agent of the present invention was prepared. The ingredients and contents (kg) are shown in Table 10.

Example 52 and 53

To water that had been heated to 80° C., one composition for blending in a finishing agent (Example 1), that had been heated to 80° C. to be dissolved homogeneously, was added with stirring to prepare emulsion. After this emulsion was cooled to 45° C. with stirring, the above-mentioned emulsion and monoethanolamine were added in order to the other composition for blending in a finishing agent (Example 28 or 29), and then mixed homogeneously with stirring. Thus, the finishing agent of the present invention was prepared. The ingredients and contents (kg) are shown in Table 10.

Example 52 and 53

TABLE 10

| | Example | | | | | | | |
|---|---|---|---|---|---|---|---|---|
| | 46 | 47 | 48 | 49 | 50 | 51 | 52 | 53 |
| composition for blending in finishing agent | Example 1 25 | Example 1 14 | Example 1 44 | Example 2 20 | Example 2 10 | Example 29 25 | Example 28 10 Example 1 10 | Example 29 40 Example 1 10 |
| additive composition | — | — | — | 2[4] | 2[4] | — | — | — |
| ethanol | — | — | — | 20 | 5 | 3 | — | — |
| phenoxyethanol | — | — | — | 0.5 | — | — | — | — |
| cetanol | — | 3.4 | — | — | — | — | — | — |
| behenyl alcohol | 1 | — | — | — | — | — | — | — |
| propylene glycol | — | — | — | — | — | 25 | — | — |
| 1,3-butylene glycol | — | — | — | 5 | 5 | — | — | — |
| neopentyl glycol dicaprate | 2 | — | — | — | — | — | — | — |
| 10% potassium hydroxide | 0.2 | — | — | — | — | 11 | — | — |

TABLE 10-continued

|  | Example | | | | | | | |
| --- | --- | --- | --- | --- | --- | --- | --- | --- |
|  | 46 | 47 | 48 | 49 | 50 | 51 | 52 | 53 |
| decamethyl cyclopentasiloxane | — | — | — | — | — | 3 | — | — |
| methyl polysiloxane | — | — | 0.5[3)] | — | — | — | — | — |
| 80% monoethanolamine | — | — | — | — | — | — | 0.6 | 2.5 |
| stearic acid | 1 | — | — | — | — | — | — | — |
| isononyl isononanoate | — | — | 5 | — | — | — | — | — |
| polyoxyethylene distearate | 0.75[1)] | — | — | — | — | — | — | — |
| stearyl trimethyl ammonium chroride | — | 0.8[2)] | — | — | — | — | — | — |
| sodium N-stearoyl-L-glutamate | — | — | 1 | — | — | — | — | — |
| hydrolyzed animal protein | — | — | — | 5[5)] | — | — | — | — |
| 1% Blue No. 1 solution | — | — | — | — | — | proper amount | — | — |
| parabens | 0.2 | 0.2 | 0.2 | — | 0.1 | 0.1 | — | — |
| water | remaining volume | remaining volume | remaining volume | remaining volume | remaining volume | 32.9 | 75 | 35 |
| total weight | 100 | 100 | 100 | 100 | 100 | 100 | 100 | 100 |

[1)–5)] in Table 10 indicates;
[1)] 140 EO,
[2)] Content; 80 wt. %,
[3)] 50 cs:3000 cs = about 1:1 (weight ratio),
[4)] ingredients (wt. %); trimethylglycine (40), 8 wt. % of dimethyl diallyl ammonium chloride · acrylamide copolymer (2.5), D-mannitol (4), methyl parahydroxybenzoate (0.1), ethanol (2), water (51.4).
[5)] 3 kg (average molecular weight, 400) + 2 kg (average molecular weight, 1000).

(Preparation of Emulsion Stabilizer)

Example 54

The composition for blending in emulsion stabilizer (Example 13) itself was used as emulsion stabilizer (Example 54). Namely, 0.9 kg of the emulsion stabilizer (Example 54), 3 kg of the composition for blending in waving agent (Example 4), 15 kg of sodium bromate and such amount of water as the total volume of the waving agent would be 100 L were added, and then mixed homogeneously with stirring. Thus, No.2 agent of waving agent of the present invention was prepared.

Then, this No.2 agent of waving agent was left at 40° C. for more than one year. As a result, it was found by visual examination that there was no change in appearance and the emulsion was stable.

(Preparation of Permanent Waving Iron Sliding Improver)

Example 55

About 99 kg of the composition for blending in permanent waving iron sliding improver (Example 27), proper amount of perfume and proper amount of aqueous colorants solution were added, and then mixed homogeneously at room temperature to prepare 100 kg of mixture. Thus, the permanent waving iron sliding improver of the present invention was prepared.

(The Organoleptic Tests about Hair Treating Effects of the Hair Treating Agents)

Hair treating were carried out to 50 monitors by the following methods. And the results of the organoleptic tests about hair treating effects (i.e. feel when used and characteristic properties) of the hair treating agents were obtained. The results of organoleptic tests were summarized in Table 11 and 12.

The Method for Hair Treating with Hair Conditioners

After ordinary shampoo, a specimen of hair conditioners (Examples 30 and 31) was applied to hair and spread by combing, and then rinsed and dried using a dryer.

The Method for Hair Treating with Hair Colorings

No.1 agent and No.2 agent of the hair coloring (Example 32 and 33) were mixed (the wt. % ratio of No.1 agents to No.2 agents was 1:1). This mixture was applied to hair and left for 30 minutes at room temperature. Then, the hair was rinsed and dried using a dryer.

The Method for Hair Treating with Waving Agents

In a Case of Curling Type Permanent Wave

No.1 agent of the waving agent (Example 34, 40~45) was applied to hair and spread by combing, and the hair was wound to a rod and left for 7 minutes at 45° C. Then No.2 agent was applied by an applicator and left for 7 minutes. Repeatedly, No.2 agent was applied by an applicator and left for 7 minutes. Next, the rod was removed, and the hair was rinsed and dried using a dryer.

In a Case of Straight Type Permanent Wave

No.1 agent of the waving agent (Example 35639) was applied to hair and spread by combing and the hair was formed to the straight shape. Then, the hair was left for 10 minutes. After that, No.2 agents (Example 35~45 and one prepared in Example 54) was applied to hair and spread by combing, further left for 10 minutes, and finally, rinsed and dried using a dryer.

The Method for Hair Treating with Finishing Agents

The finishing agent (Example 46~53) was applied to hair and spread.

The Method for Hair Treating with Permanent Waving Iron Sliding Improvers

The permanent waving iron sliding improver (Example 55) was applied to hair. And the hair was formed to predetermined hair style with iron.

TABLE 11

| feel when used and functionality | hair treating agent (Example) | | | | | | | | | | | | |
|---|---|---|---|---|---|---|---|---|---|---|---|---|---|
| | 30 | 31 | 32 | 33 | 34 | 35 | 36 | 37 | 38 | 39 | 40 | 41 | 42 |
| luster | ○ | ○ | Δ | Δ | Δ | Δ | Δ | Δ | Δ | ○ | Δ | Δ | Δ |
| smooth feel | ⊙ | ⊙ | Δ | Δ | Δ | ○ | ○ | ○ | ○ | ⊙ | Δ | Δ | Δ |
| neat feel | Δ | Δ | Δ | Δ | Δ | Δ | Δ | Δ | Δ | Δ | Δ | Δ | Δ |
| soft feel | Δ | Δ | Δ | Δ | Δ | Δ | Δ | Δ | Δ | Δ | ⊙ | Δ | ⊙ |
| moisture feel | ⊙ | ⊙ | Δ | Δ | Δ | ○ | ○ | ○ | Δ | ○ | ⊙ | ⊙ | ⊙ |
| rustle feeling | ⊙ | ⊙ | Δ | Δ | Δ | Δ | Δ | Δ | Δ | ⊙ | Δ | Δ | Δ |
| less stickiness | — | — | — | — | — | — | — | — | — | — | — | — | — |
| remained feels when waving finished | — | — | — | — | Δ | Δ | Δ | Δ | Δ | ⊙ | ○ | ○ | ○ |
| spreadability of gel | — | — | ⊙ | ⊙ | ⊙ | ⊙ | ⊙ | ⊙ | ⊙ | ⊙ | — | — | — |
| protection for hair from high temperature of iron | — | — | — | — | — | — | — | — | — | — | — | — | — |

TABLE 12

| feel when used and functionality | hair treating agent (Example) | | | | | | | | | | | |
|---|---|---|---|---|---|---|---|---|---|---|---|---|
| | 43 | 44 | 45 | 46 | 47 | 48 | 49 | 50 | 51 | 52 | 53 | 55 |
| luster | Δ | Δ | Δ | ⊙ | Δ | ⊙ | ⊙ | ⊙ | Δ | ○ | ○ | ○ |
| smooth feel | Δ | Δ | Δ | Δ | ⊙ | ⊙ | ⊙ | ⊙ | ⊙ | ⊙ | ⊙ | ⊙ |
| neat feel | ○ | Δ | ○ | ⊙ | ○ | ⊙ | Δ | Δ | ○ | ○ | ○ | Δ |
| soft feel | Δ | ○ | Δ | ○ | ⊙ | Δ | ⊙ | ⊙ | Δ | Δ | Δ | Δ |
| moisture feel | Δ | ○ | Δ | ○ | ⊙ | ○ | ⊙ | ⊙ | Δ | ○ | ○ | ○ |
| rustle feeling | ○ | Δ | Δ | Δ | Δ | ⊙ | ○ | ○ | ⊙ | ○ | ○ | ⊙ |
| less stickiness | — | — | — | ⊙ | ○ | ○ | ⊙ | ⊙ | ⊙ | ⊙ | ⊙ | — |
| remained feels when waving finished | ○ | ○ | ○ | — | — | — | — | — | — | — | — | ○ |
| spreadability of gel | — | — | — | — | — | — | — | — | ⊙ | ⊙ | ⊙ | — |
| protection for hair from high temperature of iron | — | — | — | — | — | — | — | — | — | — | — | ⊙ |

In Table 11 and 12, ⊙ indicates "very good", ○ indicates "good" and Δ indicates "normal".

As clearly understood from the results of the above-mentioned Examples, the compositions for blending in hair treating agents of the present embodiment are prepared by selecting and combining adequately the ingredients which are cheap and easy to purchase so as to display an excellent hair treating effect. Therefore, the compositions for blending in hair treating agents of the present invention may be produced by lower cost and easily.

Since the hair treating agents of the present embodiment are prepared using above-mentioned compositions for blending in hair treating agents of the present invention, the costs for production are low, further, have excellent feels when used such as luster, smooth feel, neat feel, soft feel, moisture feel, rustle feeling and less stickiness, and have excellent functionalities such as spreadability of hair treating agents and protective ability for hair etc. Further, in the preparation process of hair treating agent since, it is possible by using the compositions for blending in a hair treating agents of the present invention to blend various ingredients containing at least one compound selected from the group consisting of nonionic surfactants, silicones and polymers. etc. at a time, the production process may be remarkably simplified.

Example of the Second Embodiment

The second embodiment of the present invention is illustrated more concretely according to the following Examples.

(Preparation of the Composition for Blending in Hair Treating Agent)

Examples 56, 59~69

The amount (kg) shown in Table 13 and 14 of each ingredient was poured into a vessel and mixed, and the mixture was stirred and dissolved completely at the heating temperature shown in Table 13 and 14 (Examples 56, 59~67 and 69) or at room temperature (Example 68). Thus, the composition for blending in hair treating agent (Examples 56, 59~69) of the present invention was prepared. The ingredients and contents (kg) are shown in Table 13 and 14.

Examples 57

Polyoxyethylene oleyl ether [4.43 kg (7 EO)+1.1 kg (20EO)], lanolin and liquid petrolatum were mixed, and then heated to 93~95° C. to prepare homogeneously dissolved material. The heated homogeneously dissolved material was added with constant stirring to 25.59 L of water, that had been heated to 93~95° C., And the mixture was cooled below 28° C. to prepare homogeneous mixture.

On the other hand, lauryl trimethyl ammonium chloride, cetyl trimethyl ammonum chloride and 19.69 kg of water were mixed. After this mixture was heated to 80° C. and then mixed as stirring, this mixture was cooled below 30° C. to prepare homogeneously dissolved material (I).

Further, polyoxyethylene lanolin and 9.84 kg of water were mixed. After this mixture was heated above 80° C., and then mixed with stirring, this mixture was cooled below 30° C. to prepare homogeneously dissolved material (II).

The afore-mentioned homogeneously dissolved material (I) and (II) were added in order. Next, sorbic acid, phosphoric acid and sodium hydroxide were added. Finally, water (add water) was further added so as to adjust the total weight to be 100 kg, and mixed homogeneously. Thus, the composition for blending in hair treating agent of the present invention was prepared. The ingredients and contents (kg) are shown in Table 13 and 14.

Examples 58

Polyoxyethylene oleyl ether [2.67 kg (30 EO)+1.33 kg (50EO)] and 13.33 kg of water were mixed as stirring at 80° C. to prepare homogeneously dissolved material. Next, 13.33 kg of ice was added to the above-mentioned homogeneously dissolved material, and then the mixture was cooled below 30° C. To this, 66.67 kg of the aqueous composition[1] was added. Finally, water (add water) was further added so as to adjust the total weight to be 100 kg, and mixed homogeneously. Thus, the composition for blending in hair treating agent of the present invention was prepared. The ingredients and contents (kg) are shown in Table 13 and 14.

1) Ingredient (kg); lauryl trimethyl ammonum chloride (1.48), cetyl trimethyl ammonium chloride (9.88), polyoxyethylene oleyl ether (7.11), lanolin (4), liquid petrolatum (9), sodium hydroxide (0.06), phosphoric acid (0.01), sorbic acid (0.15), water (68.31).

TABLE 13

| | Example | | | | | | |
|---|---|---|---|---|---|---|---|
| | 56 | 57 | 58 | 59 | 60 | 61 | 62 |
| | heating temperature (° C.) | | | | | | |
| ingredient (kg) | 80 | 93~95 | 80 | 65~70 | 70~75 | 70~75 | 70~75 |
| dipolyoxyethylene oleyl methyl ammonium chloride | — | — | — | — | — | 7[1] | — |
| lauryl trimethyl ammonium chloride[2] | — | 1.47 | 0.99 | 30 | 6.8 | 15 | 40 |
| lauryl trimethyl ammonium bromide | — | — | — | — | — | — | — |
| cetyl trimethyl ammonium chloride | 2.3[3] | 9.88[4] | 6.58[4] | — | — | — | — |
| stearyl trimethyl ammonium chloride | — | — | — | — | — | — | — |
| cethyl trimethyl ammonium saccarinate | — | — | — | — | — | — | — |
| lanolin amidopropyl ethyl dimethyl ammonium ethylsulfate | — | — | — | — | — | — | — |
| polyoxyethylene lauryl ether | 10[5] | — | — | 1[6] | 3.5[6] | — | 8[6] |
| polyoxyethylene cetyl ether | 50.2[7] | — | — | — | — | — | — |
| polyoxyethylene oleyl ether | 2.5[8] | 5.53[9] | 8.74 | — | — | — | — |
| polyoxyethylene nonylphenyl ether[10] | — | — | — | — | 3.5 | — | 8 |
| polyoxyethylene castor oil | — | — | — | — | — | — | — |
| polyoxyethylene lanolin[11] | — | 2.5 | — | — | — | 1 | — |
| polyoxyethylene · polyoxypropylene lanolin | 30[12] | — | — | — | — | — | — |
| lauric acid diethanolamide | — | — | — | 3 | 0.7 | 4.5 | — |
| polyethylene glycol monolaurate | — | — | — | — | 0.5 | — | — |
| polyoxyethylene glyceryl oleate | — | — | — | — | — | — | — |
| sorbitan monolaurate | — | — | — | — | — | — | — |
| sorbitan trioleate | — | — | — | — | — | — | — |
| lanolin | — | 4 | 2.67 | — | — | — | — |
| liquid petrolatum | — | 9 | 6 | — | — | — | — |
| polyoxyethylene · methyl polysiloxane copolymer | — | — | — | — | — | — | — |
| methylphenyl polysiloxane | — | — | — | — | — | — | — |
| sodium hydroxide | — | 0.06 | 0.027 | — | — | — | — |
| phosphoric acid[13] | — | 0.01 | 0.007 | 0.04 | 0.01 | 0.06 | — |
| dibasic sodium phosphate | — | — | — | — | — | — | 0.04 |
| sorbic acid[14] | — | 0.15 | 0.1 | — | — | — | — |
| lauryl dimethlaminoacetic acid betaine | — | — | — | — | — | — | — |
| disodium edetate | — | — | — | 0.1 | 0.1 | 0.1 | 0.1 |
| hydroxyethane diphosphoric acid | — | — | — | — | — | — | — |
| polyethylene glycol | — | — | — | — | — | — | — |
| polyethylene glycol distearate | — | — | — | — | — | — | — |

TABLE 13-continued

|  | Example | | | | | | |
|---|---|---|---|---|---|---|---|
|  | 56 | 57 | 58 | 59 | 60 | 61 | 62 |
|  | heating temperature (° C.) | | | | | | |
| ingredient (kg) | 80 | 93~95 | 80 | 65~70 | 70~75 | 70~75 | 70~75 |
| phenoxyethanol | — | — | — | — | — | — | — |
| water | 5 | 67.4 | 74.89 | 65.86 | 84.89 | 72.34 | 43.86 |

[1)–14)] in Table 13 indicate,
[1)]Content, 75 wt. %, 2 EO,
[2)]Content, 30 wt. %,
[3)]Content, 70 wt. %,
[4)]Content, 50 wt. %,
[5)]4 EO,
[6)]23 EO,
[7)]2 EO:6 EO = about 1:4,
[8)]20 EO,
[9)]7 EO:20 EO = about 4:1,
[10)]11 EO,
[11)]70 EO,
[12)]50 EO, 12 PO,
[13)]Content, 85 wt. %,
[14)]Content, 85 wt. %.

TABLE 14

|  | Example | | | | | | |
|---|---|---|---|---|---|---|---|
|  | 63 | 64 | 65 | 66 | 67 | 68 | 69 |
|  | heating temperature (° C.) | | | | | | |
| ingredient (kg) | 70 | 70~75 | 70~75 | 70~75 | 70~75 | — | 80 |
| dipolyoxyethylene oleyl methyl ammonium chloride[1)] | — | 8 | 13 | — | 16 | 15 | — |
| lauryl trimethyl ammonium chloride | 35[2)] | — | — | — | — | — | — |
| lauryl trimethyl ammonium bromide | — | — | — | 20[3)] | — | — | — |
| cetyl trimethyl ammonium chloride[4)] | — | 9 | 4 | 20 | 7.4 | — | — |
| stearyl trimethyl ammonium chloride | — | — | — | — | — | 5[5)] | — |
| cethyl trimethyl ammonium saccarinate | — | — | — | — | — | — | 4.5[6)] |
| lanolin amidopropyl ethyl dimethyl ammonium ethylsulfate | — | — | — | 10[7)] | — | — | — |
| polyoxyethylene lauryl ether | 18[8)] | — | — | — | — | — | — |
| polyoxyethylene cetyl ether | — | — | — | — | — | — | — |
| polyoxyethylene oleyl ether | — | — | — | — | — | — | — |
| polyoxyethylene nonylphenyl ether | 17[9)] | — | — | 10[10)] | — | — | 40[11)] |
| polyoxyethylene castor oil | — | — | — | — | — | — | 25[15)] |
| polyoxyethylene lanolin | — | 5[12)] | 0.2[13)] | — | 0.2[14)] | — | — |
| polyoxyethylene · polyoxypropylene lanolin | — | — | — | — | — | — | — |
| lauric acid diethanolamide | 4 | — | 5 | — | 4 | — | — |
| polyethylene glycol monolaurate | — | — | — | — | — | — | — |
| polyoxyethylene glyceryl oleate | — | — | — | — | — | — | 8 |
| sorbitan monolaurate | — | — | — | — | — | 1 | — |
| sorbitan trioleate | — | — | — | — | — | — | 8 |
| lanolin | — | — | — | — | — | — | — |
| liquid petrolatum | — | — | — | — | — | — | — |
| polyoxyethylene · methyl polysiloxane copolymer | — | — | — | — | — | 12 | — |
| methylphenyl polysiloxane | — | — | — | — | — | — | 6.5 |
| sodium hydroxide | — | — | — | — | — | — | — |
| phosphoric acid[18)] | 0.04 | — | 0.08 | — | 0.08 | — | — |
| dibasic sodium phosphate | — | 0.15 | — | — | — | — | — |
| sorbic acid[14)] | — | — | — | — | — | — | — |
| lauryl dimethlaminoacetic acid betaine | — | — | — | 20 | — | — | — |
| disodium edetate | 0.1 | 0.1 | 0.1 | — | 0.1 | — | — |
| hydroxyethane diphosphoric acid | — | — | — | 0.2[16)] | — | — | — |
| polyethylene glycol | — | 5[17)] | — | — | — | — | — |
| polyethylene glycol distearate | — | — | — | — | — | — | 8 |

TABLE 14-continued

|  | Example | | | | | | |
|---|---|---|---|---|---|---|---|
|  | 63 | 64 | 65 | 66 | 67 | 68 | 69 |
|  | | | | heating temperature (° C.) | | | |
| ingredient (kg) | 70 | 70~75 | 70~75 | 70~75 | 70~75 | — | 80 |
| phenoxyethanol | — | — | — | — | — | 2 | — |
| water | 25.86 | 72.75 | 77.62 | 19.8 | 72.22 | 65 | — |

[1)–18)] in Table 14 indicate,
[1)]Content, 75 wt. %, 2 EO,
[2)]Content, 30 wt. %,
[3)]Content, 50 wt. %,
[4)]Content, 50 wt. %,
[5)]Content, 60 wt. %,
[6)]Content, 35 wt. %,
[7)]50 wt. % of dipropylene glycol,
[8)]23 EO,
[9)]11 EO,
[10)]15 EO,
[11)]9 EO,
[12)]70 EO,
[13)]20 EO,
[14)]20 EO,
[15)]10 EO,
[16)]Content, 60 wt. %,
[17)]Average molecular weight, 300~500,
[18)]Content, 85 wt. %.

(Preparation of Hair Conditioner)

Examples 70

80 kg of initial water and 2 kg of hydroxyethyl cellulose were mixed and heated to 90° C. to prepare aqueous solution. After this aqueous solution was cooled to 45° C., 10 kg of the compositions for blending in hair conditioners (Example 65) was added with stirring to the above-mentioned cooled aqueous solution, and mixed homogeneously. Thus, the hair conditioner of the present invention was prepared.

(Preparation of Waving Agent)

Example 71

Preparation of 10% Viscous Liquid 10 kg of the composition for blending in waving agent (Example 56) was heated to 80~85° C., and then homogeneously dissolved. On the other hand, 80 kg of initial water was heated to 80~85° C. The afore-mentioned heated homogeneously dissolved material was added as stirring to the heated initial water, and then homogeneously mixed. After this homogeneous mixture was cooled as stirring to 47~49° C., water was added so as to adjust the total weight to be 100 kg, and then mixed homogeneously. Thus, the viscous liquid, in which 10 wt. % of the composition for blending in waving agent was contained, was prepared.

Preparation of No.1 Agent of Waving Agent

To 25 kg of the 10% viscous liquid obtained above, 13 kg of 50% ammonium thioglycolate (ATG) and proper amount of strong ammonia solution were added at room temperature. Further, water (add water) was added so as to adjust the total weight to be 100 kg, and then mixed homogeneously. Thus No.1 agent of waving agent was prepared.

Preparation of No.2 Agent of Waving Agent 1 kg of lauryl trimethyl ammonum chloride, 8 kg of sodium bromate and water was added to prepare 100 kg of aqueous solution. This aqueous solution was used as No.2 agent of waving agent.

Example 72~82

Preparation of No.1 Agent of Waving Agent

The composition for blending in waving agent (Example 57~67), 50% ATG, strong ammonia solution and water were mixed homogeneously with stirring at room temperature. Thus, No.1 agent (Example 72~82) of waving agent was prepared. Ingredients and contents (kg) are shown in Table 15 and 16.

Preparation of No.2 Agent of Waving Agent

The composition for blending in waving agent (Example 57~59 and 67), sodium bromate and water were mixed homogeneously with stirring at room temperature. Thus, No.2 agent (Example 72~82) of waving agent was prepared. Ingredients and contents (kg) are shown in Table 15 and 16.

TABLE 15

| | Example | | | | | |
|---|---|---|---|---|---|---|
| ingredient (kg) | 72 | 73 | 74 | 75 | 76 | 77 |
| No. 1 agent | | | | | | |
| composition for blending in waving agent | Example 57<br>2 | Example 58<br>2 | Example 59<br>5 | Example 60<br>5 | Example 61<br>5 | Example 62<br>5 |

TABLE 15-continued

| ingredient (kg) | Example | | | | | |
|---|---|---|---|---|---|---|
| | 72 | 73 | 74 | 75 | 76 | 77 |
| 50% ATG | 13 | 13 | 13 | 13 | 13 | 13 |
| strong ammonia solution | proper amount | proper amount | proper amount | proper amount | proper amount | proper amount |
| water | remaining volume | remaining volume | remaining volume | remaining volume | remaining volume | remaining volume |
| total amount | 100 | 100 | 100 | 100 | 100 | 100 |
| No. 2 agent | | | | | | |
| composition for blending in waving agent | Example 57 5 | Example 58 5 | Example 59 2 | Example 59 2 | Example 59 2 | Example 59 2 |
| sodium bromate | 8 | 8 | 8 | 8 | 8 | 8 |
| water | remaining volume | remaining volume | remaining volume | remaining volume | remaining volume | remaining volume |
| total amount | 100 | 100 | 100 | 100 | 100 | 100 |

TABLE 16

| ingredient (kg) | Example | | | | |
|---|---|---|---|---|---|
| | 78 | 79 | 80 | 81 | 82 |
| No. 1 agent | | | | | |
| composition for blending in waving agent | Example 63 5 | Example 64 5 | Example 65 5 | Example 66 5 | Example 67 5 |
| 50% ATG | 13 | 13 | 13 | 13 | 13 |
| strong ammonia solution | proper amount | proper amount | proper amount | proper amount | proper amount |
| water | remaining volume | remaining volume | remaining volume | remaining volume | remaining volume |
| total amount | 100 | 100 | 100 | 100 | 100 |
| No. 2 agent | | | | | |
| composition for blending in waving agent | Example 59 2 | Example 67 2 | Example 67 2 | Example 67 2 | Example 67 2 |
| sodium bromate | 8 | 8 | 8 | 8 | 8 |
| water | remaining volume | remaining volume | remaining volume | remaining volume | remaining volume |
| total amount | 100 | 100 | 100 | 100 | 100 |

(Preparation of Finishing Agent)

Example 83

10 kg of the composition for blending in a finishing agent (Example 68), 10 L of ethanol, 0.1 kg of methyl parahydroxybenzoate, proper amount of perfume, proper amount of aromatic material dispersant and such amount of water as the total volume of the finishing agent would be 100 L were added in order with stirring, and then mixed homogeneously. Thus, finishing agent (Example 83) of the present invention was prepared.

(Preparation of Thickening Agent Used on Preparing Hair Treating Agent)

Example 84

62 kg of the composition for blending in thickening agent used on preparing hair treating agent (Example 69), 4 kg of cetyl octanoate, 12 kg of 1,3-butylene glycol and 0.1 kg of methyl parahydroxybenzoate were mixed and heated to 80° C., and then dissolved homogeneously. This homogeneously dissolved material was added with stirring to water, which had been heated to 80° C., and then dissolved homogeneously. Such amount of water as the total weight of the thickening agent used on preparing hair treating agent would be 100 kg was added. Thus, thickening agent used on preparing hair treating agent of the present invention was prepared.

30 kg of the obtained thickening agent used on preparing hair treating agent (Example 84) was added to 70 kg of the afore-mentioned waving agent (Example 59) to prepare new another type of waving agent. It was confirmed by visual inspection that the waving agents had changed from fluid state to gel stage. Further, the organoleptic tests of this new type of waving agent were carried out as follows. The results of organoleptic tests were summarized in Table 17.

(The Organoleptic Tests About Hair Treating Effects of the Hair Treating Agents)

Hair treating were carried out to 50 monitors by the following methods. And the results of the organoleptic tests about hair treating effects (i.e. feel when used and characteristic properties) of the hair treating agents were obtained. The results of organoleptic tests were summarized in Table 17.

The Method for Hair Treating with Hair Conditioners

After ordinary shampoo, a specimen of hair conditioners (Examples 70) was applied to hair and spread by combing, and then rinsed and dried using a dryer.

The Method for Hair Treating with Waving Agents

In a Case of Curling Type Permanent Wave

No.1 agent of the waving agent (Example 71~82) was applied to hair and spread by combing, and the hair was wound to a rod and left for 7 minutes at room temperature. Then No.2 agent was applied by an applicator and left for 7 minutes. Repeatedly, No.2 agent was applied by an applicator and left for 7 minutes. Next, the rod was removed, and the hair was rinsed and dried using a dryer.

In a Case of Straight Type Permanent Wave

No.1 agent of the waving agent (new type of waving agent prepared in Example 84) was applied to hair and spread by combing and the hair was formed to the straight shape. Then, the hair was left for 10 minutes. After that, No.2 agent was applied to hair and spread by combing, further left for 10 minutes, and finally, rinsed and dried using a dryer.

The Method for Hair Treating With Finishing Agents

The finishing agent (Example 83) was applied to hair and spread.

Since the hair treating agents of the present embodiment are prepared using above-mentioned compositions for blending in hair treating agents of the present invention, the costs for production are low, further, have excellent feels when used such as moisture feel, smooth feel, slightly oily feel, pleasant sense of touch to the hair, luster, suppleness, soft feel and smooth combing, and have excellent functionalities such as less hair damage (protective ability for hair), absorptivity to hair•penetrating ability into hair•adhesiveness to hair•spreadability of hair treating agent (especially waving agent), moisturizing ability, smooth formation of less uneven, firmly rooted and knitted wave and prevention against generation of static electricity etc. Further, in the preparation process of hair treating agent since it is possible by using the compositions for blending in a hair treating agents of the present invention to blend cationic surfactants and nonionic surfactants etc. at a time, the production process may be remarkably simplified.

What is claimed is:

1. A composition blended in a hair treating agent, comprising:
polyoxyethylene oleyl ether,
sorbitan monooleate,
methylphenyl polysiloxane,
dimethysiloxane•methylstearoxysiloxane copolymer

TABLE 17

| feel when used and functionality | hair treating agent (Example) | | | | | | | | | | | | | |
|---|---|---|---|---|---|---|---|---|---|---|---|---|---|---|
| | 71 | 72 | 73 | 74 | 75 | 76 | 77 | 78 | 79 | 80 | 81 | 82 | 83 | 84 |
| moisture feel | ⊙ | ○ | ○ | △ | △ | △ | △ | △ | ○ | ○ | ⊙ | ⊙ | △ | ○ |
| smooth feel | ⊙ | △ | △ | △ | △ | △ | △ | △ | △ | △ | △ | △ | ⊙ | △ |
| slightly oily feel | △ | ⊙ | ⊙ | △ | △ | △ | △ | △ | ○ | ⊙ | △ | ⊙ | △ | △ |
| pleasant sense of touch to the hair | ○ | ⊙ | ⊙ | ○ | ⊙ | ○ | △ | △ | ⊙ | ⊙ | ⊙ | ⊙ | ○ | ○ |
| luster | △ | △ | △ | △ | △ | △ | △ | △ | ⊙ | ○ | △ | ⊙ | ⊙ | △ |
| suppleness | △ | ○ | △ | △ | ○ | ○ | ○ | △ | ⊙ | ○ | ⊙ | ○ | △ | ⊙ |
| softening effect | △ | ○ | △ | ○ | ⊙ | ⊙ | ⊙ | △ | ○ | ⊙ | ⊙ | ⊙ | △ | ○ |
| smooth combing | ○ | ○ | ○ | △ | △ | △ | △ | △ | ⊙ | ○ | ○ | ○ | ⊙ | ○ |
| less hair damage | △ | ⊙ | ⊙ | △ | △ | △ | △ | △ | △ | ○ | ○ | — | ○ | △ |
| absorptivity to hair | — | — | — | — | — | — | — | — | — | — | — | — | ⊙ | — |
| penetrating ability into hair | ⊙ | ⊙ | ⊙ | ⊙ | ⊙ | ⊙ | ⊙ | ⊙ | ⊙ | ⊙ | ○ | ⊙ | — | ○ |
| moisturizing ability | ⊙ | ⊙ | ⊙ | ⊙ | ⊙ | ⊙ | ⊙ | ⊙ | ○ | ○ | ○ | ○ | — | ○ |
| smooth wave formation | ○ | ⊙ | ⊙ | ⊙ | ⊙ | ⊙ | ⊙ | ○ | ○ | ○ | ○ | ○ | — | ⊙ |
| less uneven wave | △ | ⊙ | ⊙ | ○ | ○ | ⊙ | ○ | ○ | ○ | ○ | ○ | ○ | — | ○ |
| firmly rooted wave | ○ | ⊙ | ⊙ | ○ | ○ | ⊙ | ○ | ○ | ⊙ | ○ | ○ | ○ | — | ○ |
| adhesiveness and spreadability | ○ | ○ | ○ | ○ | ○ | ⊙ | ○ | ○ | ⊙ | ⊙ | ○ | ⊙ | — | ○ |
| knitting of wave | ○ | ○ | | △ | △ | △ | △ | △ | ⊙ | ○ | ○ | ○ | — | △ |
| improving the hold of waves | ⊙ | △ | △ | ⊙ | ⊙ | ⊙ | ○ | ○ | ○ | ○ | ○ | △ | — | ○ |
| prevention against generation of static electricity | △ | ○ | ○ | △ | △ | △ | ○ | ○ | ⊙ | ⊙ | ⊙ | ○ | — | ⊙ |

In Table 17 and 12, ⊙ indicates "very good", ○ indicates "good" and △ indicates "normal".

As clearly understood from the results of the above-mentioned Examples, the compositions for blending in hair treating agents of the present embodiment are prepared by selecting and combining adequately the ingredients which are cheap and easy to purchase so as to display an excellent hair treating effect. Therefore, the compositions for blending in hair treating agents of the present invention may be produced by lower cost and easily.

liquid petrolatum,
sorbic acid,
phosphoric acid,
sodium hydroxide and
water.

2. A composition blended in a hair treating agent, comprising:
polyoxyethylene oleyl ether,
sorbitane monooleate,
polyoxyethylene sorbitane monooleate, liquid petrolatum,
chlorinated paraffin,
sorbic acid,
phosphoric acid,
sodium hydroxide and
water.

3. A composition blended in a hair treating agent, comprising:
polyoxyethylene oleyl ether,
sorbitane monooleate,
mink oil,
liquid petrolatum,
oleic acid,
sorbic acid,
phosphoric acid,
sodium hydroxide and
water.

4. A composition blended in a hair treating agent, comprising:
polyoxyethylene oleyl ether,
sorbitane monooleate,
liquid petrolatum,
chlorinated paraffin,
oleic acid,
sorbic acid,
phosphoric acid,
sodium hydroxide and
water.

5. A composition blended in a hair treating agent, comprising:
polyoxyethylene oleyl ether,
sorbitane monooleate,
liquid petrolatum,
chlorinated paraffin,
sorbic acid,
phosphoric acid,
sodium hydroxide and
water.

6. A composition blended in a hair treating agent, comprising:
polyoxyethylene lauryl ether,
styrene polymer emulsion,
2-alkyl-N-carboxymethyl-N-hydroxyethyl imidazolinium betaine,
cocoyl amide propyldimethyl glycine,
phosphoric acid and
water.

7. A composition blended in a hair treating agent, comprising:
polyoxyethylene oleyl ether,
sorbic acid,
phosphoric acid,
sodium hydroxide and
water.

8. A composition blended in a hair treating agent, comprising:
polyoxyethylene lauryl ether,
2-alkyl-N-carboxymethyl-N-hydroxyethyl imidazolinium betaine,
cocoyl amide propyldimethyl glycine,
phosphoric acid and
water.

9. A composition blended in a hair treating agent, comprising:
oleic acid diethanolamide,
triethanolamine polyoxyethylene lauryl ether sulfate,
lauric acid,
cocoyl amide propyldimethyl glycine,
triethanolamine,
1-hydroxyethane-1,1-diphosphonic acid,
methyl parahydroxybenzoate and
water.

10. A composition blended in a hair treating agent, comprising:
polyoxyethylene polyoxypropylene glycol,
polyethylene glycol,
ammonium polyoxyethylene lauryl ether sulfate,
dibasic sodium phosphate,
disodium edetate,
methyl parahydroxybenzoate and
water.

11. A composition blended in a hair treating agent, comprising:
methyl polysiloxane and
aminoethylaminopropylsiloxane•dimethysiloxane copolymer.

12. A composition blended in a hair treating agent, comprising:
carboxyvinylpolymer,
phosphoric acid,
monobasic sodium phosphate,
1-hydroxyethane-1,1-diphosphonic acid and
water.

13. A composition blended in a hair treating agent, comprising:
carboxyvinylpolymer,
phosphoric acid,
1-hydroxyethane-1,1 diphosphonic acid and
water.

* * * * *